United States Patent [19]

Peckham et al.

[11] Patent Number: 5,167,229
[45] Date of Patent: Dec. 1, 1992

[54] FUNCTIONAL NEUROMUSCULAR STIMULATION SYSTEM

[75] Inventors: Paul H. Peckham; Brian Smith, both of Cleveland Hts.; James R. Buckett, Avon; Geoffrey B. Thrope, University Hts.; Jorge E. Letechipia, Shaker Hts., all of Ohio

[73] Assignee: Case Western Reserve University, Cleveland, Ohio

[21] Appl. No.: 843,159

[22] Filed: Mar. 24, 1986

[51] Int. Cl.⁵ .............................................. A61N 1/36
[52] U.S. Cl. .................................. 128/421; 128/419 R
[58] Field of Search ............... 128/419 R, 421–423; 339/48, 205; 623/10; 604/175

[56] References Cited

U.S. PATENT DOCUMENTS

| | | | |
|---|---|---|---|
| 2,521,722 | 9/1950 | Hubbell et al. | 439/732 |
| 3,067,401 | 12/1962 | Rhodes | 439/723 |
| 3,568,675 | 3/1971 | Harvey | 604/355 |
| 3,663,965 | 5/1972 | Lee, Jr. et al. | 623/11 |
| 3,701,080 | 10/1972 | Baisz et al. | 439/289 |
| 3,850,161 | 11/1974 | Liss | 128/422 |
| 3,964,470 | 6/1976 | Trombley | 604/175 |
| 4,019,518 | 4/1977 | Maurer et al. | 128/419 |
| 4,223,679 | 9/1980 | Schulman | 128/419 PT |
| 4,250,882 | 2/1981 | Adair | 604/355 |
| 4,281,664 | 8/1981 | Duggan | 128/419 PT |
| 4,453,162 | 6/1984 | Money et al. | 128/419 PT |
| 4,459,989 | 7/1984 | Borkan | 128/421 |
| 4,528,987 | 7/1985 | Slocum | 128/903 |
| 4,532,932 | 8/1985 | Batty, Jr. | 128/419 PT |
| 4,558,704 | 12/1985 | Petrofsky | 128/423 R |
| 4,561,443 | 12/1985 | Hogrefe et al. | 128/903 |
| 4,569,352 | 2/1986 | Petrofsky et al. | 128/423 W |
| 4,579,120 | 4/1986 | MacGregor | 604/175 |
| 4,586,510 | 5/1986 | Glaser et al. | 128/423 |
| 4,622,973 | 11/1986 | Agrawala | 128/421 |
| 4,632,116 | 12/1986 | Rosen et al. | 128/419 R |
| 4,639,667 | 1/1987 | Andresen | 340/870.33 |
| 4,640,983 | 2/1987 | Comte | 128/784 |
| 4,645,504 | 2/1987 | Byers | 604/175 |

FOREIGN PATENT DOCUMENTS

| | | | |
|---|---|---|---|
| 8601733 | 3/1986 | France | 128/421 |
| 1181671 | 9/1986 | U.S.S.R. | 128/421 |
| 945482 | 1/1964 | United Kingdom | 339/205 |
| 2085733 | 5/1982 | United Kingdom | 128/421 |

OTHER PUBLICATIONS

"Design and Control of a Manipulator for Tetraplegics" by Paeslack et al.; Mechanism & Machine Theory 1977, vol. 12, No. 5, pp. 413–423.

"Coordinated Two-Mode Graspin the Qudraplegic Initiated by Functional Neuromuscular Stimulation".

(List continued on next page.)

Primary Examiner—David M. Shay
Attorney, Agent, or Firm—Fay, Sharpe, Beall, Fagan, Minnich & McKee

[57] ABSTRACT

An input command controller (A) provides logic function selection signals and proportional signals. The signals are generated by movement of a ball member (12) and socket member (14) relative to two orthogonal axes. When the joystick is implanted, a transmitter (50) transmits the signals to a patient carried unit (B). The patient carried unit includes an amplitude modulation algorithm such as a look-up table (124), a pulse width modulation algorithm (132), and an interpulse interval modulation algorithm (128). The algorithms derive corresponding stimulus pulse train parameters from the proportional signal which parameters are transmitted to an implanted unit (D). The implanted unit has a power supply (302) that is powered by the carrier frequency of the transmitted signal and stimulation pulse train parameter decoders (314, 316, 318). An output unit (320) assembles pulse trains with the decoded parameters for application to implanted electrodes (E). A laboratory system (C) is periodically connected with the patient carried unit to measure for changes in patient performance and response and reprogram the algorithm accordingly. The laboratory system also performs initial examination, set up, and other functions.

6 Claims, 15 Drawing Sheets

OTHER PUBLICATIONS

"Programmed Six Channel . . . During Walking", by P. Strojnik et al.; IEEE Trans. on Biomed. Eng., vol. BME-26, No. 2, Feb. 79, pp. 112-116.

"Proportionally Controlled Functional Electrical Stimulation of the Hand", by S. Rebersek et al.; Arch Phys Med Rehabil, vol. 54, Aug. 1973, pp. 378-382.

"EMG Controlled Functional . . . of the Paretic Hand" by G. Hansen; Scand J. Rehab Med 11, 1979, pp. 189-193.

"Control of Movements by Functional Neuromuscular Stimulation" by P. Crago, Eng in Med & Biol Magazine, Sep. 1983, pp. 32-36.

"Electronic Detours of Broken Nerve Paths", by L. Vodovnik et al.; Electronics, Sep. 20, 1965, pp. 110-116.

"An Implantable RF Powered Dual Channel Stimulator", by C. Poon et al.; Biotelemetry Patient Monitg, vol. 8, No. 3, 1981, pp. 180-188.

"Remote Monitoring . . . in Unrestrained Cats", by Prochazka et al., Electroencephalography & Clin. Neurophysiology, vol. 37, No. 6, Dec. 1974, pp. 649-653.

"Mobility Aid for Quadriplegics", by Maass et al.; 1973 Carnahan Conference on Electronic Prosthesis; Lexington, Ky., 19-21 Sep. 1973, pp. 123-125.

"Theoretical Design . . . for Neural Prosthesis Applications", by Forster; J. Biomed. Eng., vol. 3, No. 2, Apr. 1981, pp. 107-120.

"Design and Fabrication for Experimental Cochlear Prosthesis", by Leob et al., Med & Biomed Eng & Comput, May 1983, pp. 241-253.

"Restoration and Hand Function in the Quadriplegic Through Electrical Stimulation", by P. Peckham & J. T. Mortimer from Functional Electrical Stimulation ed. by Hanbrecht and Reswick, Marcel Dekker, Inc. 1977, pp. 83-95.

"A Portable Microprocessor Controlled Implantable Functional Neuomuscular Stimulation System", by B. Smith, S. D. Braswell, J. Buckett, K. Jackson, P. Peckham from Proceedings of the 2nd Int. Conf. on Rehab. Eng. 1984.

"Closed Loop Control of Force During Electrical Stimulation of Muscle", by P. Crago, J. Mortimer, and P. Peckham from IEEE Transactions on Biomedical Engineering, vol. MBE 27, No. 6, Jun. 1980, pp. 306-312.

"Multichannel Implantable Stimulator for Control of Paralyzed Muscle", by P. Peckham, C. Poon, W. Ko, E. Marsolais and J. Rosen from IEEE Transaction on Biomedical Engineering, vol. BME 28, No. 7, Jul. 1981, pp. 530-536.

"A Computer-Controlled Multichannel Stimulation System for Laboratory Use in Functional Neuromuscular Stimulation", Geoffrey B. Thrope, P. H. Peckham, and P. E. Crago; IEEE Transactions on Biomedical Engineering, vol. BME-32, No. 6, Jun. 1985, pp. 363-370.

"A Microprocessor Based Portable Functional Electrical Stimulation System", by J. R. Bucklett, S. D. Braswell, G. B. Thrope, P. H. Peckham; 6th Annual Conference on Rehabilitation Engineering, San Diego, Calif. 1983, pp. 72-74.

"Controlled Prehension and Release in the C5 Quadriplegic Elicited by Functional Electrical Stimulation of the Paralyzed Forearm Musculature", by P. H. Peckham, J. T. Mortimer, and E. B. Marsolais; Annals of Biomedical Engineering, vol. 8, pp. 369-388, 1980.

"Restoration of Key Grip and Release in the C5 and C6 Tetraplegic Through Functional Electrical Stimulation", by P. H. Peckham, A. A. Freehafer, R. B. Strother, G. B. Thrope; Proceedings of International Conference on Rehabilitation Engineering-Toronto, Canada 1980, pp. 227-229.

"Shoulder Position Control, An Alternative Control Technique for Motion Impaired Individuals", by J. R. Buckett, P. H. Peckham, and R. B. Strother; Proceedings of International Conference on Rehabilitation Engineering, Toronto, Canada 1980, pp. 244-247.

"Alteration in the Force and Fatigability of Skeletal Muscle in Quadriplegic Humans Following Exercise Induced by Chronic Electrical Stimulation", by P. H. Peckham, J. T. Mortimer, and E. B. Marsolais; Clinical Orthopaedics and Related Research; No. 114, Jan.-Feb. 1976, pp. 326-334.

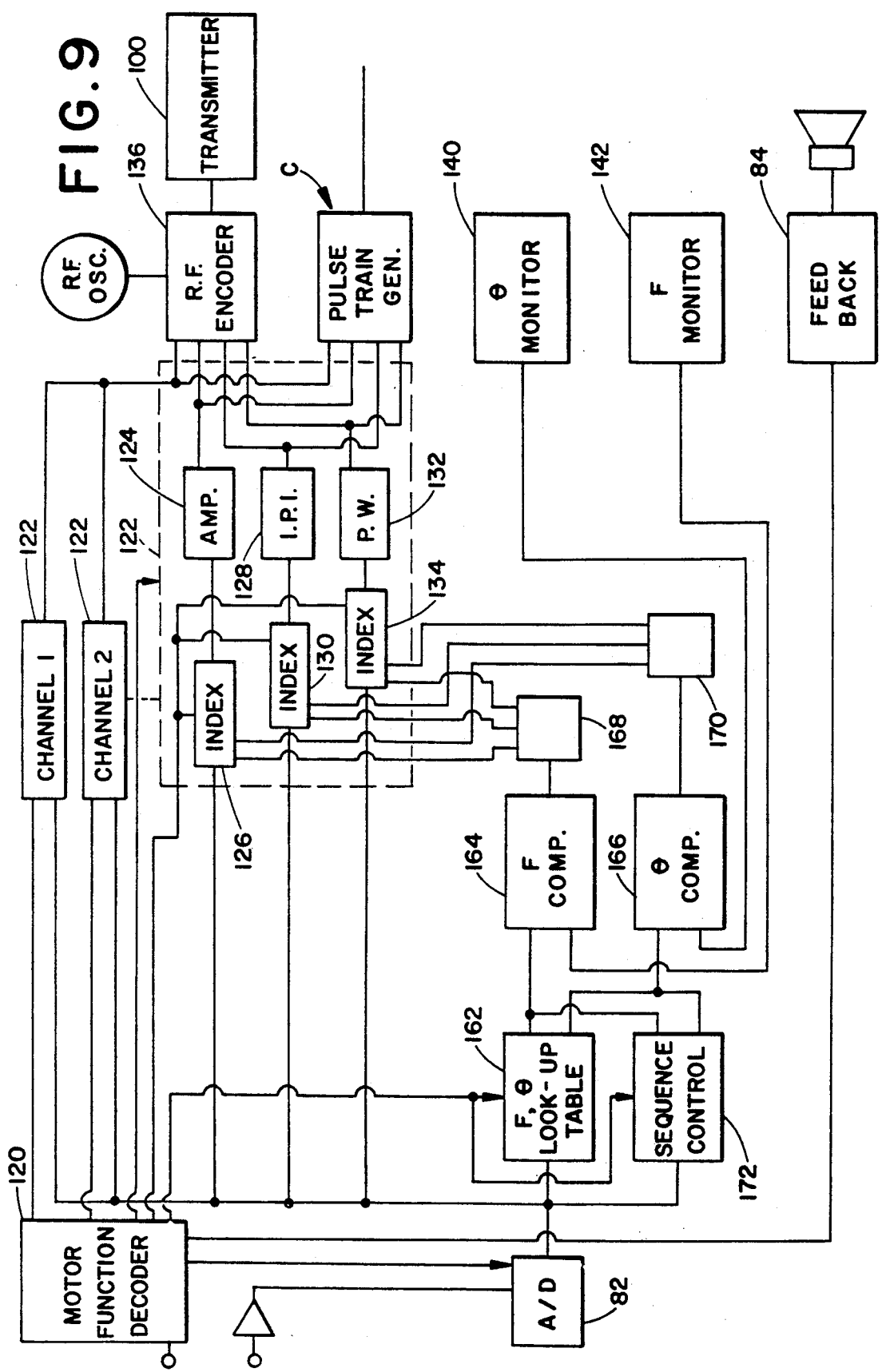

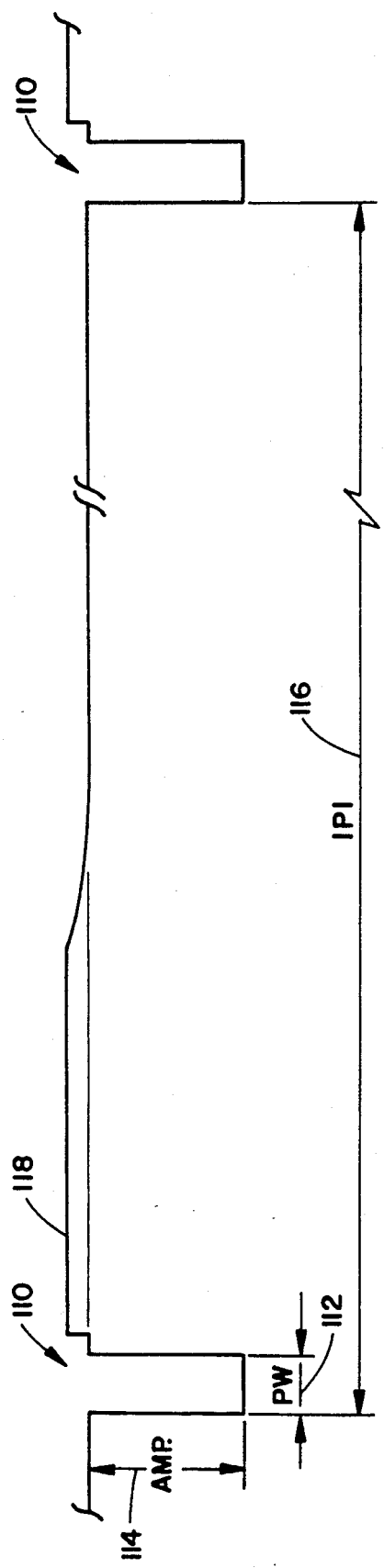

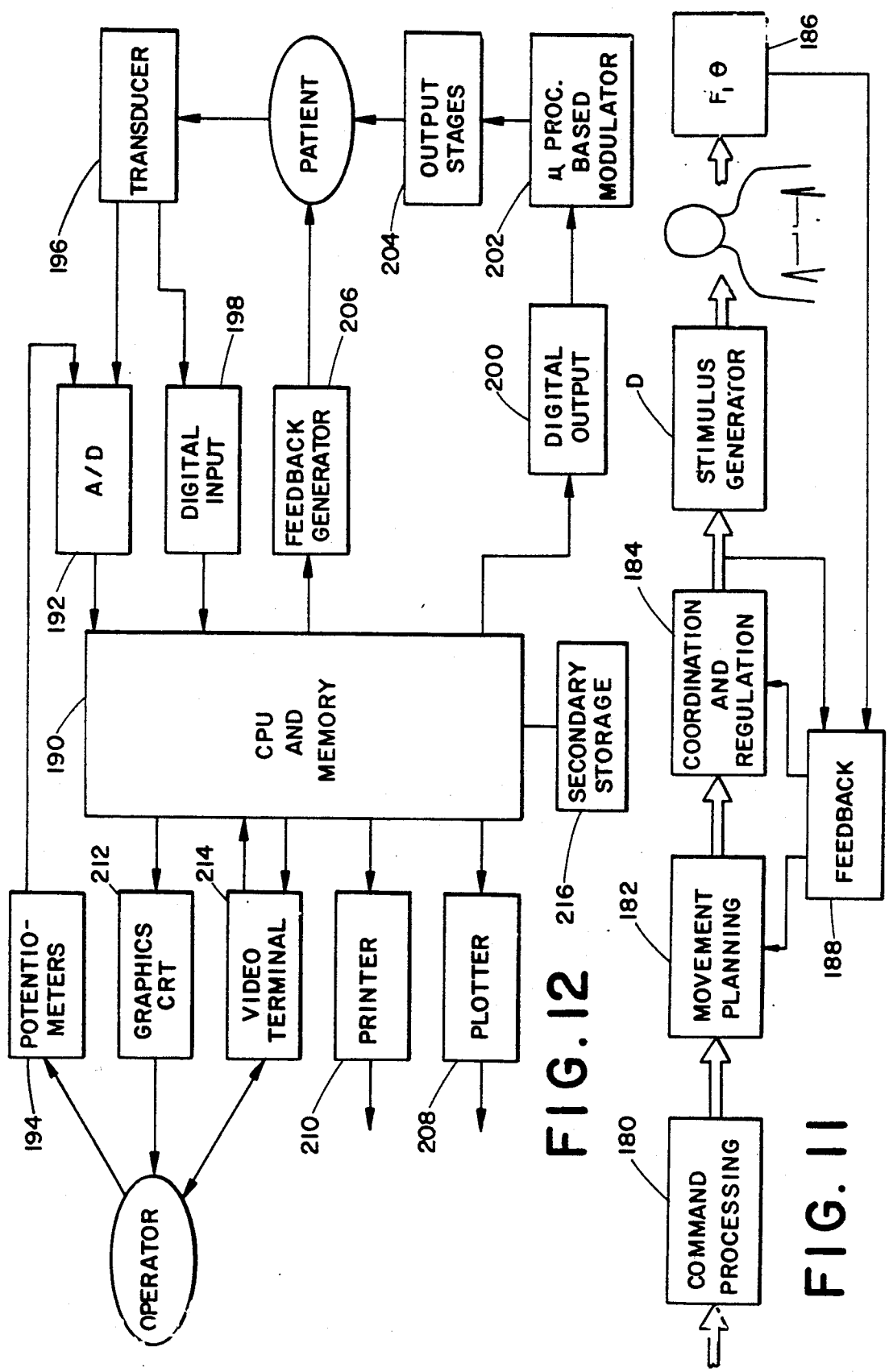

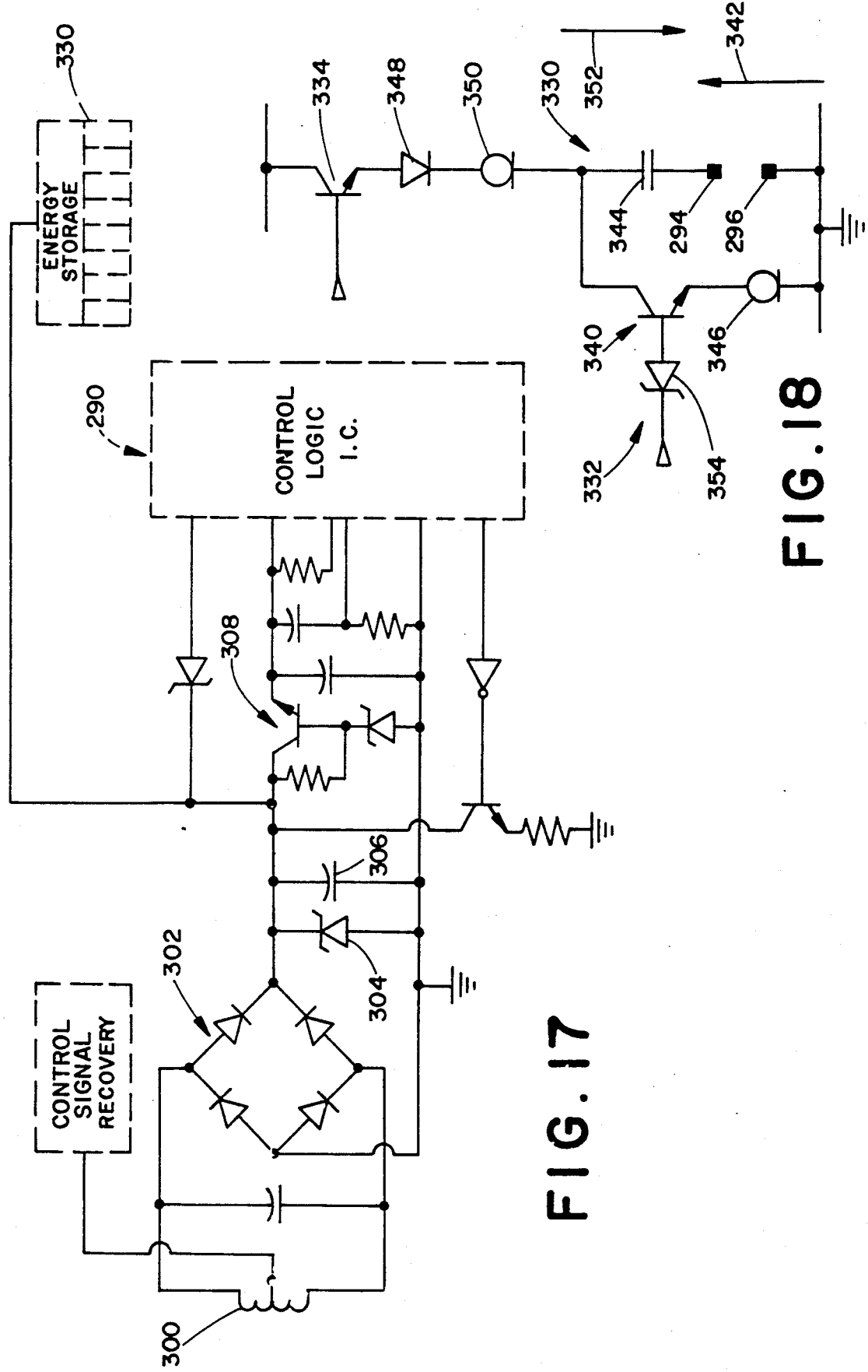

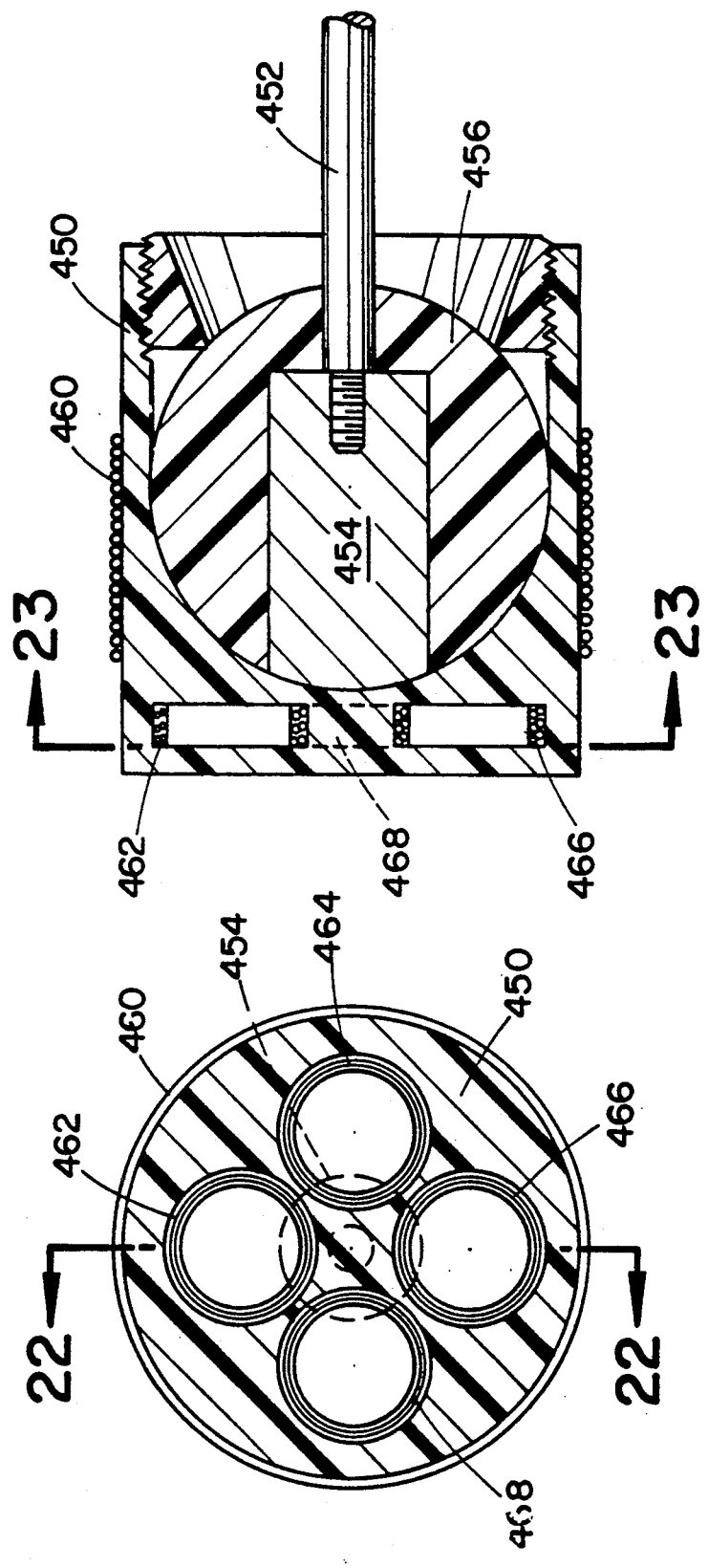

5,167,229

FUNCTIONAL NEUROMUSCULAR STIMULATION SYSTEM

BACKGROUND OF THE INVENTION

The present invention relates to the art of functional neuromuscular stimulation. It finds particular application in providing hand control functions in central nervous system (CNS) disabilities such as quadraplegia and stroke victims and will be described with particular reference thereto. However, it is to be appreciated that the invention is also applicable to providing locomotive and control of other lower body functions in CNS disabled victims and to providing control of other muscles over which the patient has lost partial or full voluntary control.

In healthy humans, electrical signals originate in the brain and travel through the spinal cord and subsequently to peripheral nerves to a muscle which is to be contracted. More accurately, the signals travel to two or more muscles whose contractions apply forces antagonistically to a joint structure. The relative forces determine the degree and speed of movement. By appropriately applying the electrical stimulation to various muscles, a wide degree of voluntary movement can be achieved. In injuries to the CNS, the passage of electrical signals through the injured area may be disrupted. Commonly, lower spinal cord injuries will terminate the transmission of electrical control signals to muscles in the lower part of the body. Damage to the upper part of the spinal cord may block the flow of voluntary muscular control signals to upper and lower body regions. For example, in an upper spinal column injury at the C6 vertebrae, which is frequently injured in accident victims, muscular control below the elbows is commonly lost.

As early as 1791, Luigi Galvani produced artificial contractions in the muscle of frogs' legs by the application of electrical potentials. In the ensuing years, electrical stimulation therapy has been greatly refined. Cardiac pacemakers, for example, have become commonplace.

Several different groups of researchers have enabled paraplegic patients to stand and walk with walkers or crutches by applying preselected sequences to surface electrodes over their leg muscles. Surface stimulation is satisfactory for some walking and other less detailed movements. However, with surface electrodes, it is difficult to make an accurate selection of the muscle to be stimulated or an accurate prediction of the strength of the stimulus signal reaching the muscle.

Surgically implanted electrodes provide accurate selection of the muscle to be stimulated. Further, the stimulation remains more consistent over a long period of time. This renders implanted electrodes advantageous for the more delicate and complex motion associated with hands.

Numerous experimental systems have been devised and implemented to provide computer controlled electrical stimulation to the muscles of the legs, arms, and hands of patients. These experimental systems are commonly large and bulky. Frequently, the patient must be connected with a personal computer or other small computer by a cable or tether. Although smaller, dedicated computer systems could be designed, the larger programmable computer systems are generally preferred for experimental flexibility. The response to a given stimulus varies widely among patients and over time within each patient. The larger programmable computer facilities customizing for different patients and changes in a given patient.

The present invention provides a new and improved functional neuromuscular stimulation system which increases patient independence and performance.

SUMMARY OF THE INVENTION

In accordance with the aspect of the present invention, a functional neuromuscular stimulation system is provided. An input command means provides a command control signal which is indicative of a selected physiological movement or group of movements. A first parameter processing means derives the parameters of a first stimulus pulse train from the control signal. The first parameter processing means includes an amplitude means for selecting amplitude of each stimulation pulse of the pulse train, an interval means selects an interpulse interval between pulses of the pulse train and a pulse width means selects a pulse width for each pulse of the pulse train, each in accordance with the control signal. A pulse train generation generates a pulse train with the selected amplitude, interpulse interval, and pulse width. An electrode is connected with the pulse train generator for applying the pulse train to a muscle to be stimulated.

In accordance with a more limited aspect of the present invention, a plurality of similar parameter processing means are provided for uniquely deriving additional stimulation of pulse trains from the control signal(s) for application to additional electrodes implanted at other locations in the same or other muscles.

In accordance with another more limited aspect of the present invention, a physiological parameter monitor is provided for monitoring a preselected parameter of physiological movement, such as position or force. A parameter comparing means compares the monitored parameters with a parameter value retrieved from a preprogrammed look-up table. Any difference between the monitored and retrieved prameters is determined. At least one of the amplitude, interpulse interval, and the pulse width of the stimulus pulse train are adjusted such that the difference is minimized.

In accordance with another aspect of the present invention, a Hall-effect command control signal generator is provided. A permanent magnet is mounted in a ball member, such as in an externally worn device or surgically implanted, e.g. in the clavical of the patient. A first pair of Hall-effect plates are mounted in a socket member, such as external device or the sternum of the patient to define an axis. At least one additional Hall-effect plate is mounted in the socket member to define a second axis. A power supply provides a current flow in one direction across each of the Hall-effect plates. A potential difference monitoring means monitors the potential difference generally transverse to the first direction across each Hall-effect plate to provide an output signal indicative of the change of potential thereacross. In this manner, as the permanent magnet moves relative to the Hall-effect plates, the change in their relative proximity causing corresponding changes in the magnetic flux density across each plate which causes corresponding changes in the path of current flow along said one direction, hence the potential difference across the Hall-effect plates. In this manner, the output signals from the potential difference monitoring means are indicative of the angular position of the ball and socket member relative to the first and second axes.

In accordance with another aspect of the invention, a joystick includes a ferrite core mounted in a ball member. The ball member is rotatably mounted in a socket member. A driving coil is connected with the socket member encircling at least a portion of the ferrite core. A plurality of sensing coils are mounted to the socket member adjacent the ferrite core such that the transfer of an input signal from the driving coil to each of the sensing coils is controlled by the relative proximity between the ferrite core and the sensing coils.

In accordance with another aspect of the invention an implanted telemetry system is provided. An antenna receives a radio frequency signal which is converted into electromotive power by a power supply. An encoding means encodes an electrical signal which controls a gate means. The gate means selectively connects a load across the antenna to modulate a characteristic thereof such that a monitorable characteristic of the radio frequency signal is also modulated by the load.

In accordance with another aspect of the present invention, a laboratory system customizes electrical stimulus pulses to the patient. The system includes a command processing means for providing control parameters indicative of selected command functions and degrees of movement. A movement planning means derives movement parameters indicative of preselected movement, force, or other motion related parameters of the controlled limb in response to each control parameter. A coordination and regulation means derives appropriate stimulus parameters from the motion parameters. A stimulus generator assembles an appropriate electrical stimulus pulse train in accordance with the stimulus parameters.

In accordance with a more limited aspect of the present invention, a comparing means is provided for comparing actual physical motion parameters achieved by the patient's limb being controlled and the selected motion parameters of the movement planning means. The stimulus parameters selected by the coordination regulation means are automatically adjusted in order to bring the actual and selected motion parameters into optimal coincidence.

In accordance with another aspect of the present invention, a multichannel implanted stimulator system is provided. The stimulator system includes an antenna for receiving a carrier signal which is moudulated with channel, pulse width, and pulse amplitude information for one or more of the channels. A power supply means derives operating voltage for other system components from the carrier signal. A decoding means decodes at least selected channel, pulse width, and pulse amplitude information from the modulations. For each channel, an energy storage means is provided for providing energy for a current pulse from the power supply through the muscle tissue between a stimulating electrode and a reference electrode. A channel selection means selects the appropriate channel and corresponding stimulating electrode to which an electrical pulse of the decoded pulse width is to applied. A current regulating means regulates the amplitude of the pulse in accordance with the decoded amplitude.

In accordance with another aspect of the invention, the implanted stimulus system includes a metal capsule which defines a hermetically sealed chamber therein. A receiving antenna receives signals indicative of the stimuli to be applied to electrodes. Electrical circuitry is mounted in the capsule for converting received radio frequency signals into stimulus pulses. A plurality of electrical leads are electrically connected with the circuitry and the electrodes and mechanically connected with the capsule.

In accordance with another aspect of the invention, an electrical lead construction for implanted electrodes is provided. First and second lengths of multi-strand wire are wrapped helically around a longitudinal axis of the lead. A flexible polymeric insulator material encapsulates the helically wound wires.

In accordance with another aspect of the present invention, a shield assembly is provided for protecting a percutanesous interface. A shield member includes a peripheral lip portion extending peripherally around a central shield member portion. The central shield member portion is constructed of a resilient elastomeric material with a low profile. An aperture is defined through the central shield member for alignment with a point at which electrical wires pass through the patient's skin. An electrical connector which is operatively connected with the electrical lead wires passing through the patient's skin is mounted to the shield member central section. An overlay member having an aperture which conforms with the shield member central portion overlays the shield member and is adhesively adhered to the shield member peripheral lip portion and to the patient's skin around the shield member.

One advantage of the present invention is that it is readily customized to an individual patient. Moreover, the customization can be altered and refined as the patient becomes more proficient with the apparatus, as the patient's muscle become stronger, and the like.

Another advantage of the present invention resides in its portability.

Yet, another advantage of the present invention resides in the ease with which operators can adapt it to an individual patient.

Still further advantages of the present invention will become apparent to those of ordinary skill in the art upon reading and understanding the following detailed description of the preferred embodiments.

BRIEF DESCRIPTION OF THE DRAWINGS

The invention may take form in various steps and arrangements of steps and in various parts and arrangements of parts. The drawings are only for purposes of illustrating a preferred embodiment of the invention and are not to be construed as limiting it.

FIG. 8 is a diagrammatic illustration of an exemplary muscle stimulation electrical pulse sequence in accordance with the present invention;

FIG. 9 is a further block diagram of the patient-carried unit of FIG. 7;

FIG. 10 is diagrammatic illustration of thumb and finger extension, flextion, and force as a function a proportional command signal during a stimulated thumb and forefinger gripping motion;

FIG. 11 is a diagrammatic illustration of the data handling stages of the laboratory system;

FIG. 12 is a hardware configuration of a laboratory system which interfaces with the patient-carried stimulator;

Figure 16:
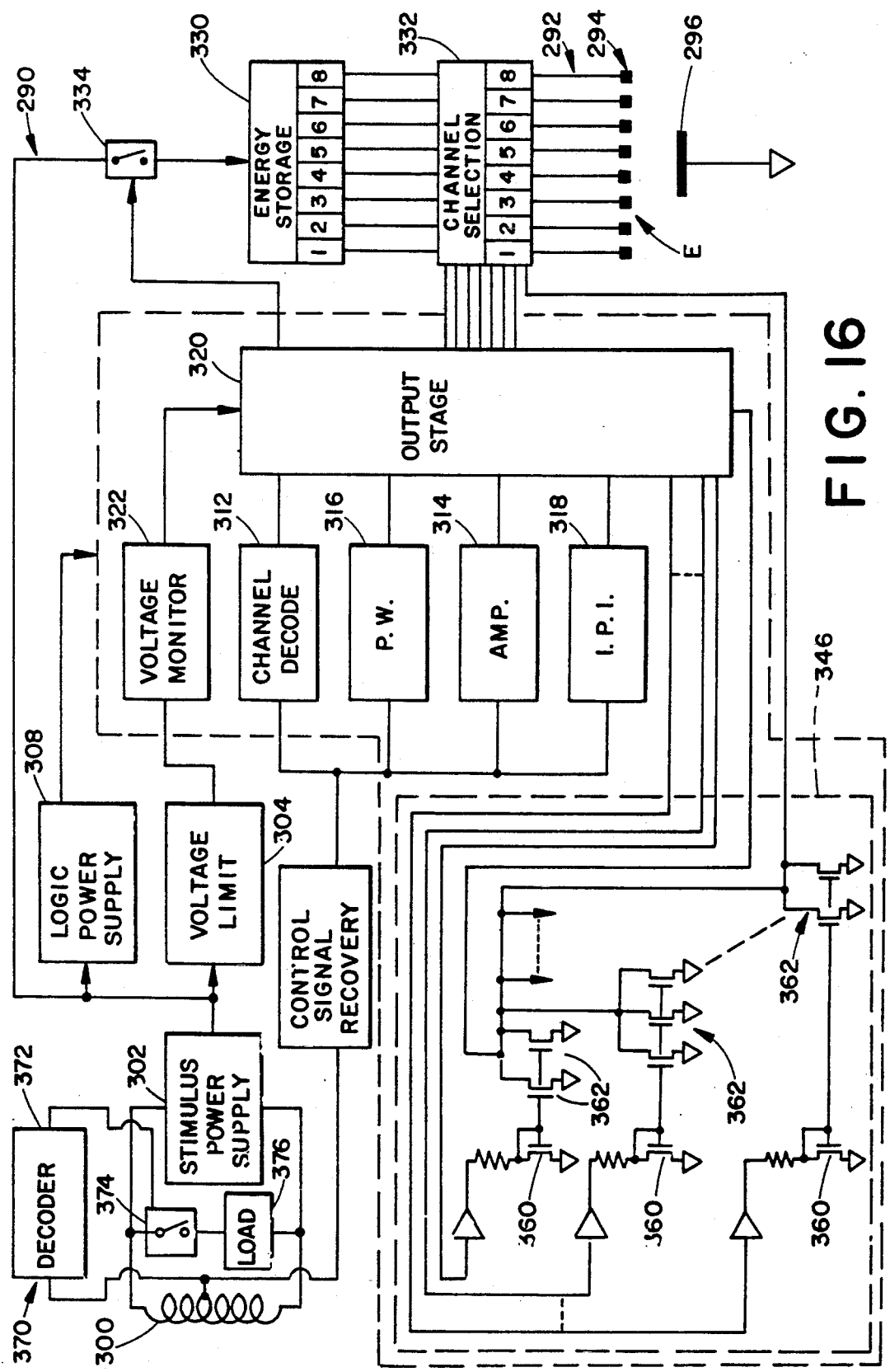
Figure 19:
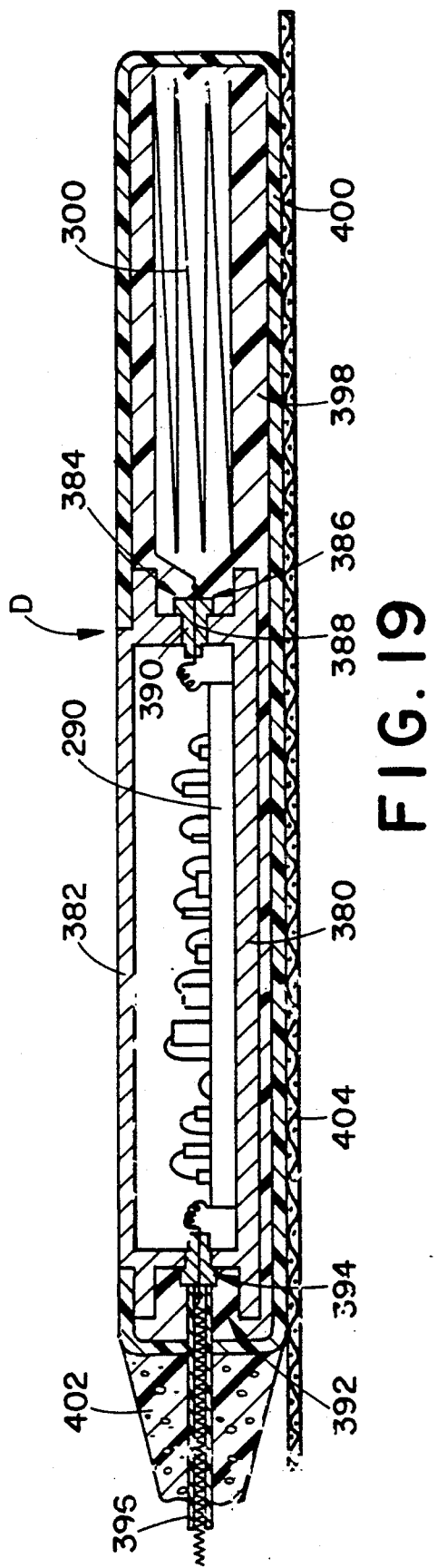
Figure 20:
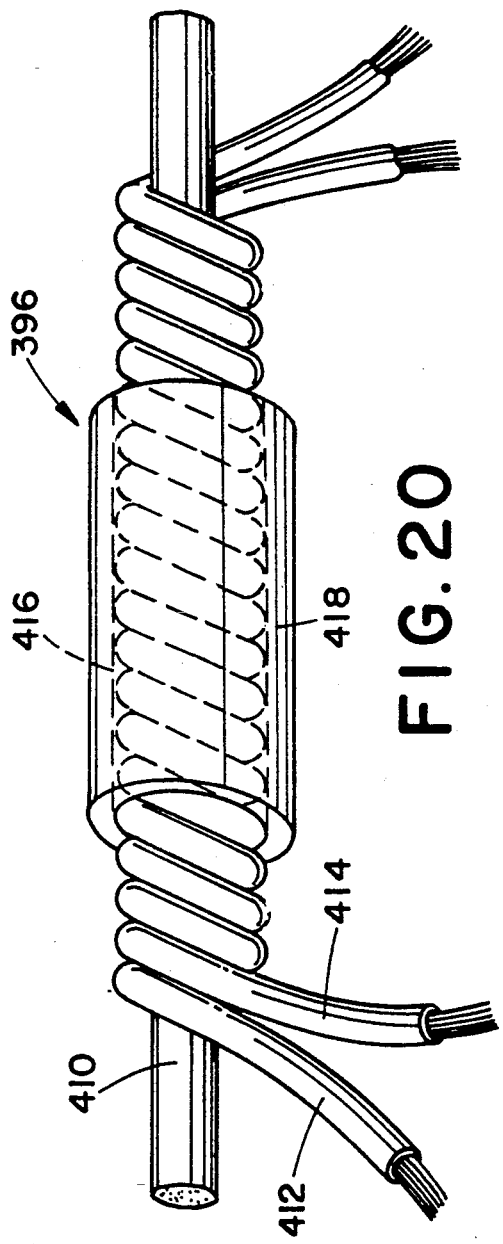
Figure 21:
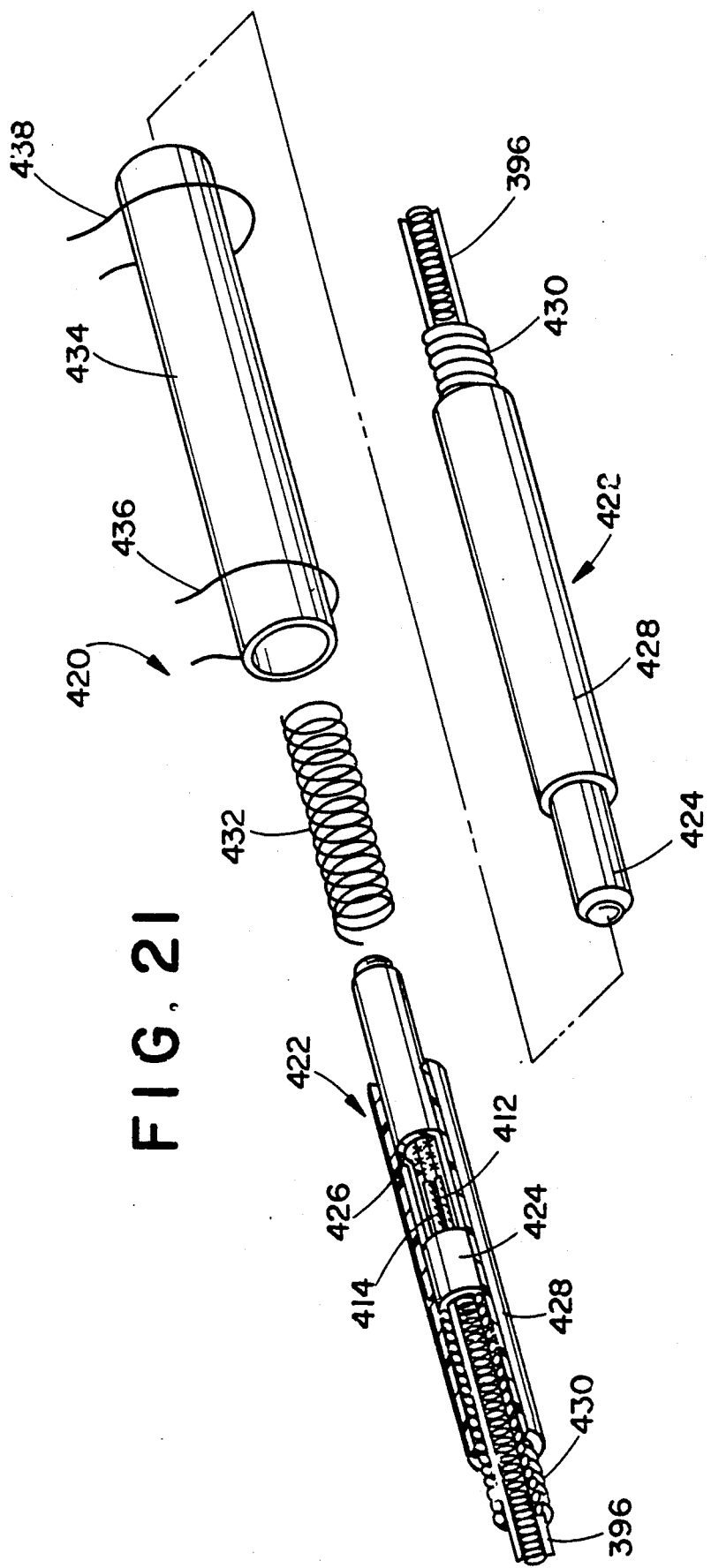
Figure 24:
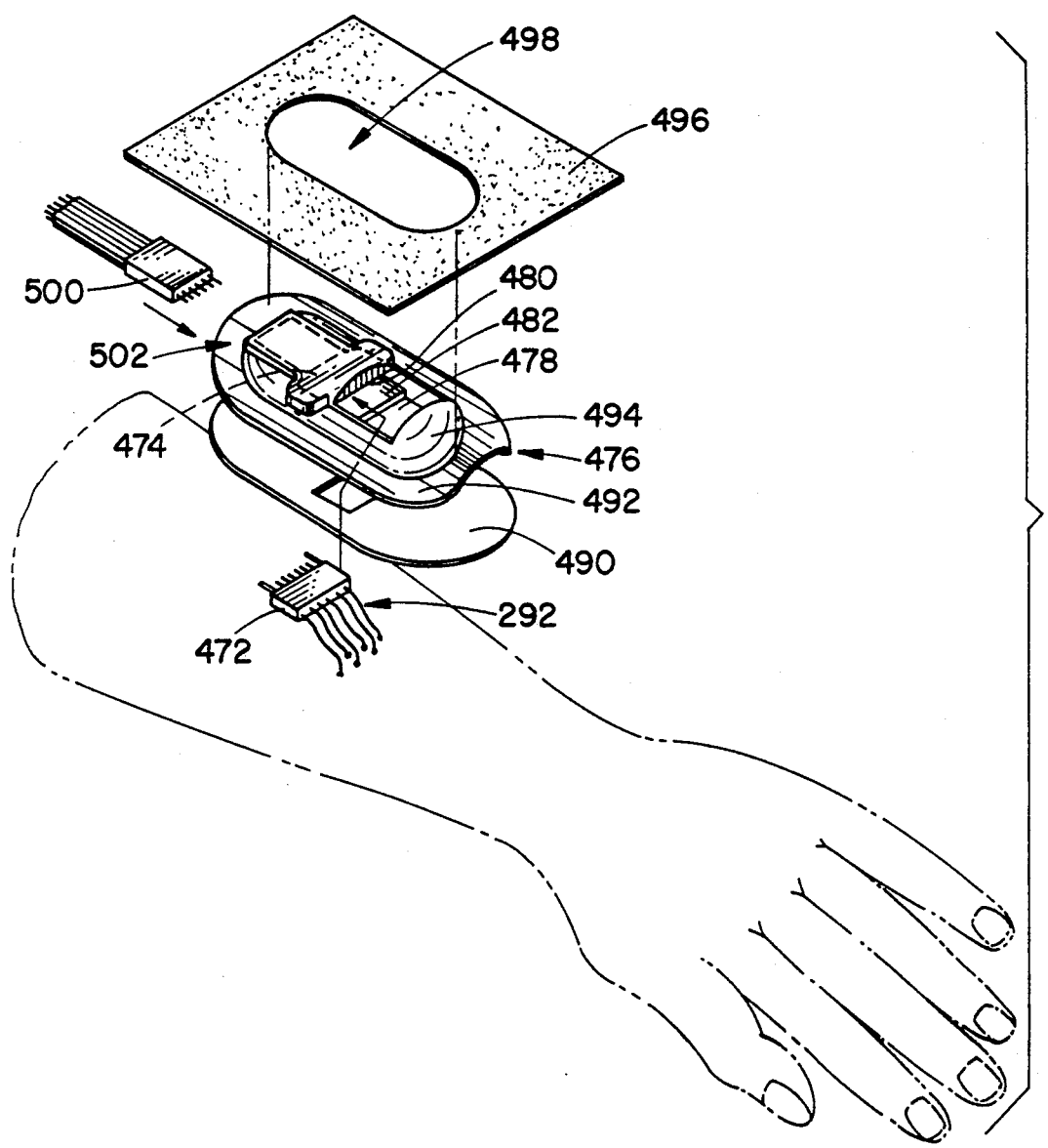

FIGS: 13, 14, and 15 are diagrams of data processing in the laboratory system of FIG. 12;

FIG. 16 is a diagrammatic illustration of an implanted stimulator for stimulating implanted electrodes;

FIG. 17 is a detailed diagram of the power supply of the implanted stimulator;

FIG. 18 is a detailed illustration of the circuitry for applying electrical pulses through muscle tissue between a stimulus and a reference electrode;

FIG. 19 is a side sectional view of the implanted stimulator illustrating the mechanical encapsulation thereof;

FIG. 20 illustrates electrode lead wire construction;

FIG. 21 is an expanded view of a lead wire connector;

FIG. 22 is a side sectional view of an alternate embodiment of a joystick in accordance with the present invention;

FIG. 23 is a sectional view of the joystick of FIG. 22 taken through section 23—23; and, FIG. 24 is an expanded, perspective view of a percutaneous interface.

DETAILED DESCRIPTION OF THE PREFERRED EMBODIMENT

Figure 2:
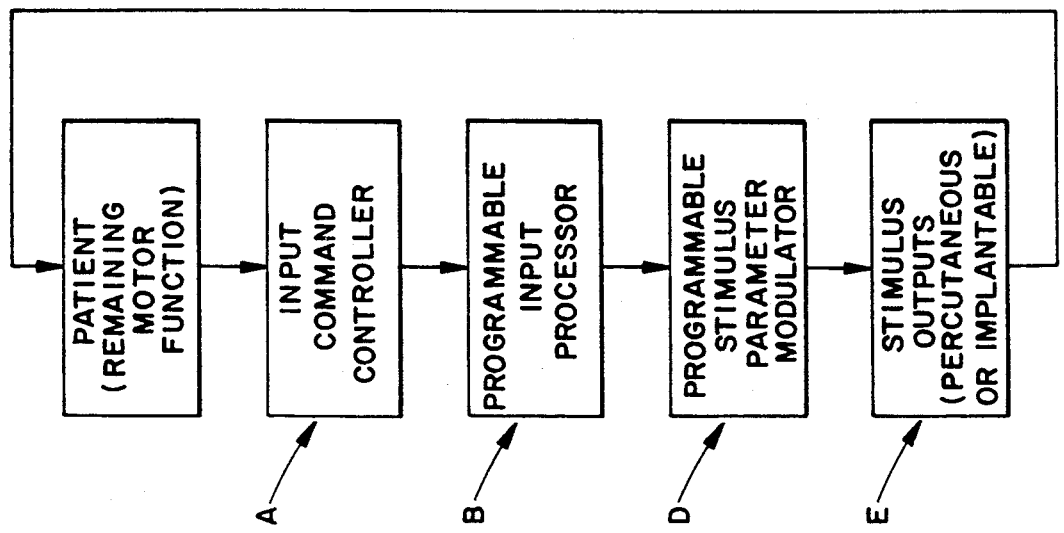
FIG. 2 is a block diagram of a functional neuromuscular stimulation system in accordance with the present invention.
Figure 1:
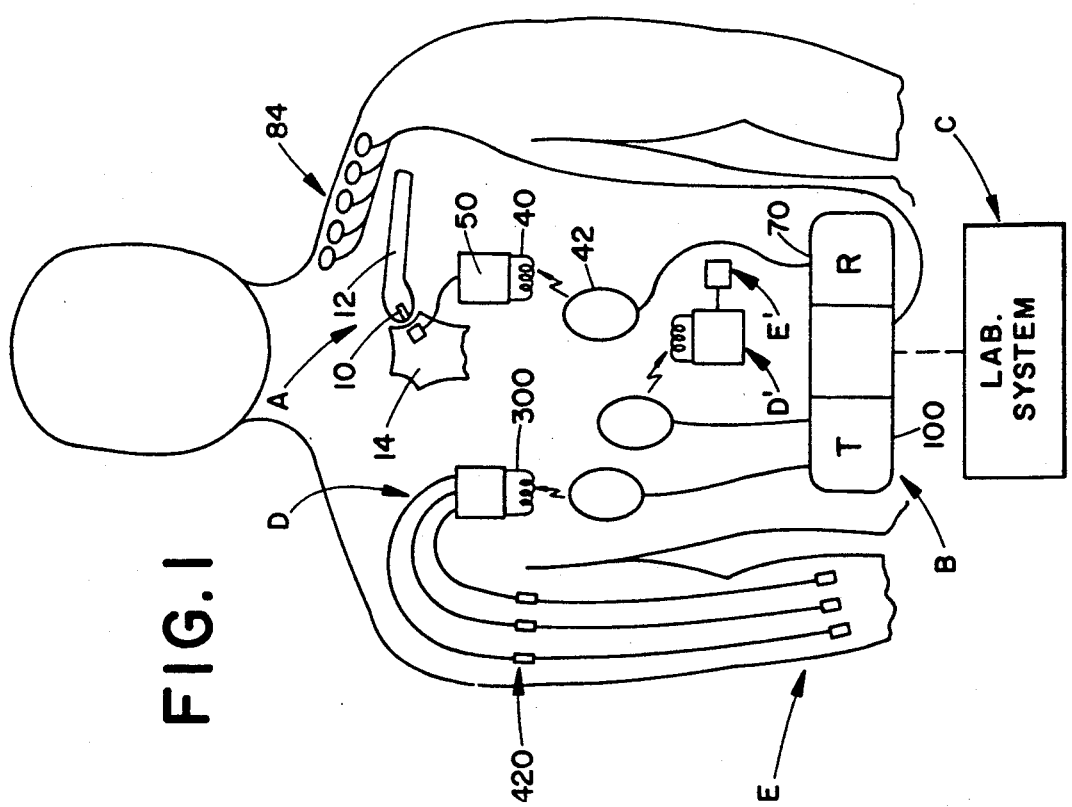
FIG. 1 is a diagrammatic illustration of the present invention in combination with a user.

With reference to FIGS. 1 and 2, an input command control means A produces electrical command control signals for controlling the limb or muscles in question. The input commands are derived from remaining voluntary functions of the patient, e.g. shoulder. In the preferred embodiment, the input control means provides both function selection or logic signals and proportional signals in response to shoulder movement of the patient. The function selection signal selects the motor function to be performed, such as turning the system on or off, freezing the stimulus parameters applied to the patient's hand, selecting among a preselected group of gripping or other hand motions, and the like. The proportional signal indicates a selected degree of the physical movement or force. In this manner, the patient can accurately control the progress of the selected movement, the position of the hand, arm or other limb, the strength of a grip, and the like.

A portable, patient-carried control system or means B receives the function selection and proportional signals from the input command means A. From the received signals, the portable control system selects the appropriate electrodes to receive electrical stimulation and the appropriate electrical stimulation signals for each electrode. More specifically, the portable control means B selects the pulse width, interpulse interval, amplitude, or other characteristics of an electrical stimulation signal or pulse train in accordance with the proportional signal. The portable system selects appropriate electrodes, algorithms or conversion factors between the proportional signal and stimulation signal parameters, internal control functions, and the like in response to the received function selection signals.

A central or laboratory reprogramming means or system C selectively reprograms the portable system B. The reprogramming adjusts the relationship between the proportional signal and the electrical stimulus signals, alters the internal control functions, and otherwise customizes the portable system to the patient. As the patient's muscle tone and strength improve with the continued use, the operating parameters of the portable control system B are reprogrammed and refined. Further, the central means C analyzes the performance of the portable system for potential failures or defects, accumulates and analyses historical data, provides physical therapy instructions, derives data of therapeutic value to the operator, provides training routines, and the like.

In the preferred embodiment, the portable control means B only selects the appropriate electrical stimulation pulse train parameters. A first implanted stimulator means D under the control of the portable system B applies the electrical signals to first implanted electrodes E to control a first body function, such as hand movement. A second implanted stimulator D' selectively receives control signals from the portable system B and applies electrical signals to one or more second implanted electrodes E' to control a second body function, such as bladder control. Additional implants may also be provided. Preferably, each implant has an interrogatable identification which is interrogated by the portable unit B. The portable unit correlates the transmitting channels with the corresponding implanted unit. This self correcting feature saves the patient the inconvenience of matching a dedicated transmitting antenna with a specific implant. Alternately, the portable system may be connected directly with the electrodes E through a percutaneous interface.

Figure 3:
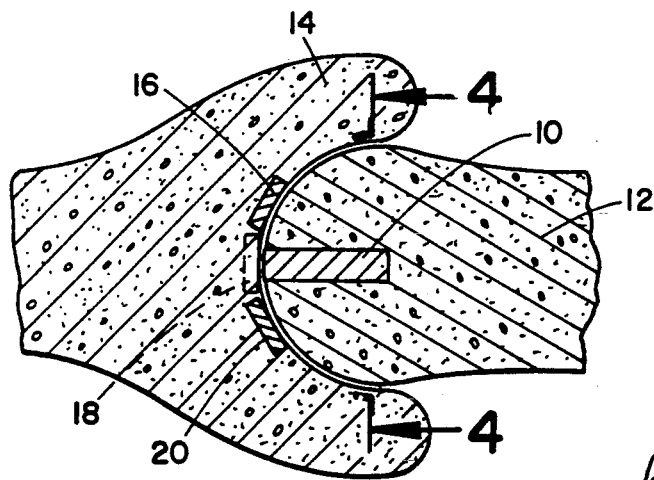
FIG. 3 is a side sectional view of a Hall-effect joystick in accordance with the present invention.
Figure 4:
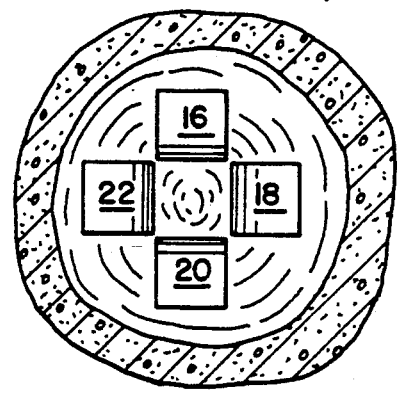
FIG. 4 is a view of the socket of FIG. 2 through section 4—4.

With continuing reference to FIG. 1 and particular reference to FIGS. 3 and 4, one of the preferred embodiments of the input command control means A is provided. The input command control means is mounted to be controlled by the shoulder of the patient opposite to the hand which is to be controlled. To control the right hand, the input control is mounted for movement by the left shoulder. A permanent magnet 10 is imbedded in a ball member, preferably surgically implanted in the clavical 12 of the patient. In a matching socket joint 14, preferably in the sternum, four Hall-effect transducer plates 16, 18, 20, and 22 are surgically mounted. Hall plates 16 and 20 are mounted along a first axis which is orthogonal to a second axis along which Hall elements 18 and 22 are mounted. Preferably, the Hall elements are mounted in coordination with the axes along which the patient has the greatest, most controllable shoulder motion. It is to be appreciated that other numbers of plates may be used. For example, three plates can define two axes. Even two plates can define the relative position of the ball member and socket, but with an ambiguity. In some applications, proper placement of the plates and signal processing circuitry may be able to resolve the ambiguity adequately.

Figure 5:
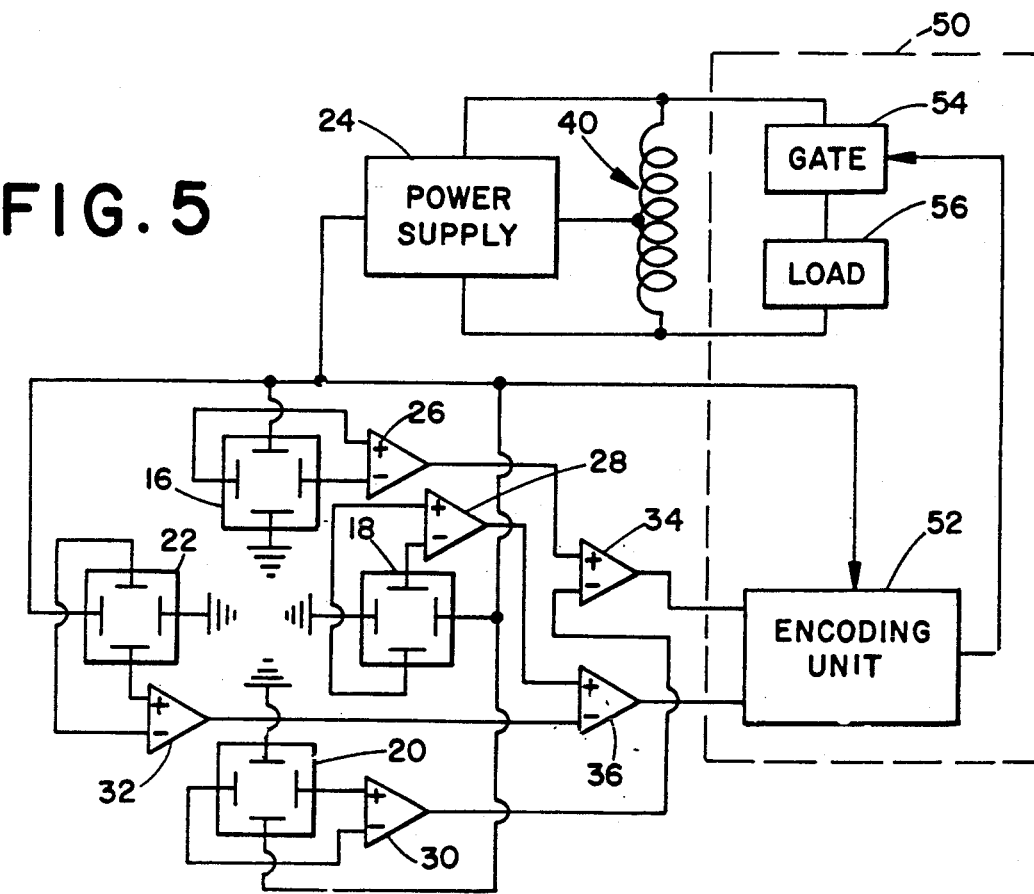
FIG. 5 is a circuit diagram of the Hall-effect joystick and a transmitter for transmitting joystick position information to the patient exterior.

With reference to FIG. 5, each Hall element is a conductive plate across which a current is induced flowing from a power regulator 24 to ground. In accordance with the Hall-effect, the current passing through the conductive plate is deviated toward the side of the plate in the presence of magnetic flux from the permanent magnet 10. This deviation causes a change in the potential difference between the sides of the plate which is proportional to the magnetic flux density through the element which, in turn, varies with the proximity of the permanent magnet 10 thereto. Differential amplifiers 26, 28, 30, and 32 are each associated with one of the Hall-effect plates to measure the potential change thereacross.

A first axis differential amplifier 34 differentially combines the output of differential amplifiers 26 and 30 to produce a first axis analog signal which is proportional to motion of the permanent magnetic relative to the first axis. A second axis differential amplifier 36 is connected with the Hall elements to provide a second axis analong output signal which varies in proportion to the position of the permanent magnetic along the second axis.

In the preferred embodiment, the output signal from the Hall elements along the axis along which the patient has the greatest range of movement provides the proportional signal and the output signal from along the other axis provides the function selection or logic signal. In the preferred embodiment, the function is changed in response to the function selection signal making a sudden change in amplitude of at least a preselected duration.

Optionally, an accelerometer may be mounted in the patient's shoulder and the output of the accelerometer may provide the function selection signal. Proportional control signals may then be provided corresponding to two axes. As yet another option, the Hall-effect elements and the permanent magnet may be mounted in a ball and socket joint of man-made construction. The two portions of the man-made ball and socket joint are selectively connected with portions of the shoulder, either externally or implanted.

With continuing reference to FIG. 5, the power supply 24 is connected with a receiving antenna 40 which is irradiated with a radio frequency signal applied external to the patient by a power transmitting cord 42 of the portable unit B. The received signal, in the preferred embodiment about 10 MHz., induces currents in receiving antenna 40 which are converted to motive power by the power supply 24.

A telemetry unit 50 receives the first and second analog outputs of the Hall-effect joystick for transmission to the portable processor B. The telemetry unit includes an encoding means 52 which encodes the first axis signal from amplifier 34 and the second axis signal from amplifier 36 into a preselected digital format. Optionally, analog formats may also be implemented. The ones and zeroes of the encoded digital signal control a gate means 54 which selectively applies a load 56 across the receiving coil 40. The applied load changes the characteristics in a manner which can be sensed by the power transmitting coil 42 and the portable unit B. Alternately, the encoded signal from the telemetry unit 50 may be transmitted on a carrier frequency for reception by a receiving coil of the portable unit B. As another alternative, direct electrical connection can be utilized, particularly if the joystick is mounted to the patient externally.

In a typical functional interactive system operation, electrical communication is established between the input command controller A and the portable unit B. In the preferred embodiment, making this connection first prevents the unit from going into the exercise mode. Second, an electrical interconnection is established between the portable unit B and the implanted electrodes E. The system powers up to an idle mode which is a non-stimulating low power consumption state.

In the preferred embodiment, the patient depresses a switch mounted adjacent to the shoulder position transducer to commence operation. The system goes into a grasp mode selection scan in which feedback cues indicate which grasp mode is indicated. Releasing the chest switch or performing another preselected operation, such as shifting the shoulder vertically, stops the scanning in the disired grasp mode.

During a short delay, the patient positions his shoulder forward and aft at a desired zero set point. The portable unit sets itself with the selected position as the zero or null set point between plus and minus ranges of motion. It is to be appreciated that if the operator does not select the center of his physical movement range, significantly greater control will be provided in one direction of movement than in the other. After the set point selection delay, the system turns on in a functional mode with the defined set point representing a zero level of command. Shoulder movement from the set point, in turn, proportionally controls the selected grasp.

Rapid movement along the axis orthogonal to the proportional axis initiates a hold or lock mode which maintains a constant stimulus output independent of shoulder position. To exit the hold mode, another rapid movement allows the user to regain proportional control after realigning the shoulder to the position it was in along the proportional control axis when the hold was initiated. This provides a smooth transition from the hole mode to the proportional control mode without disrupting the grasp. Feedback cues, such as audio tones, indicate the state of operation to the user. To place the system in idle mode, the user depresses and releases the chest mounted switch.

Figure 6:
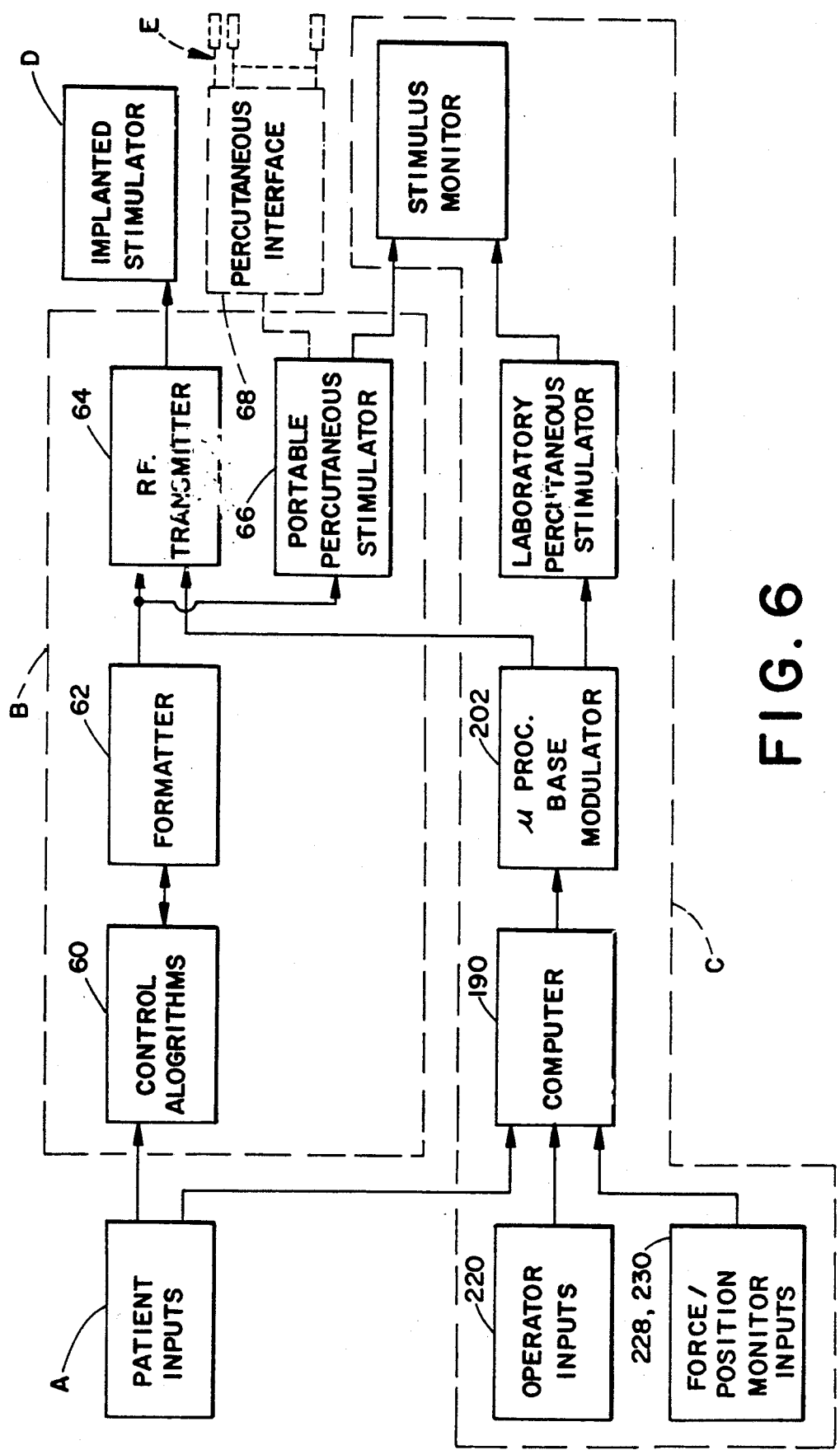
FIG. 6 is a block diagram of the interaction between a patient-carried unit and a laboratory system.

With particular reference to FIG. 6, the signals from the input command controller A are operated on by control algorithms 60 which operate on the proportional signals with algorithms which select muscles to be stimulated and electrical pulse stimulation characterisitics for each muscle. A formating means 62 formats the stimulation pulse train characterisitics to an appropriate format to be transmitted by radio frequency transmitter 64 to the implanted stimulator D. A portable percutaneous stimulator 66 enables the formated control signals to be applied directly to the electrodes E through a percutaneous interface 68.

Referring again to FIG. 1, the patient-carried control B includes a receiver 70 for receiving the function selection and proportional signals, i.e. the first and second axis signals. When the input control is externally mounted or when the interconnection is by way of a percutaneous interface, electrical wires directly connect the patient carried control B and the input control means A. When the input control means is implanted and the patient-carried control system is externally carried, they are interconnected by the telemetric interface 50.

Figure 7:
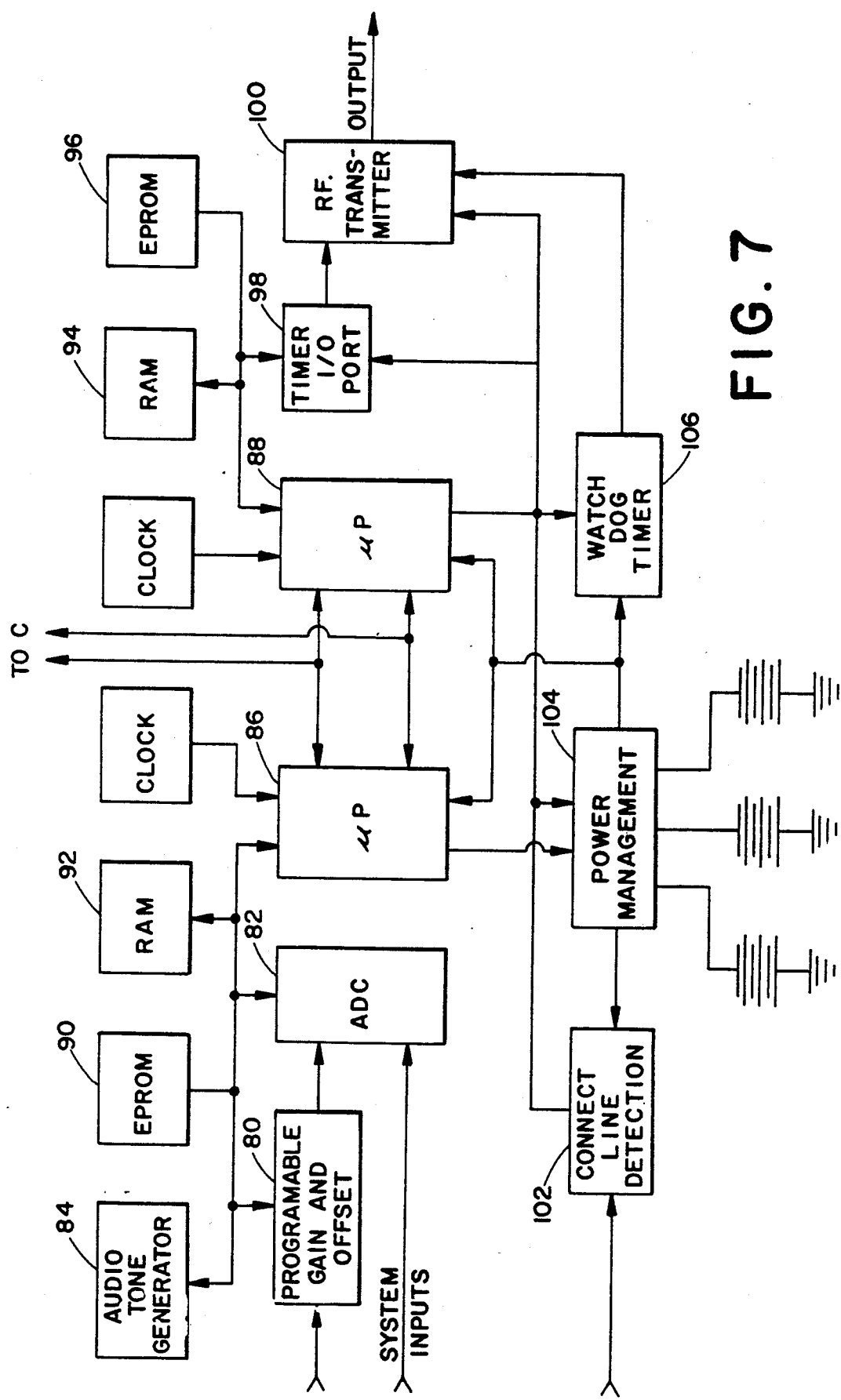
FIG. 7 is a hardware diagram of a patient-carried microprocessor base control unit of the stimulator system of FIG. 1.

With reference to FIG. 7, a programmable gain and offset means 80 selectively adjusts the gain and an offset for an analog proportional signal to bring it into the appropriate range for an analog to digital converter 82. The function selection signal is conveyed directly to selected channels of the analog to digital converter 82.

With digital received signals, the gain and offset means and the analog to digital converter are eliminated.

A feedback means 84 provides the patient with feedback regarding the state of the portable unit, e.g. selected grapsing mode, on/off state, locking mode, the position of the null set point, or the like. The feedback means 84 may be a tone generator, an electrocutaneous system such as a shoulder mounted electrodes 84 of FIG. 1, or the like. The electrocutaneous feedback is advantageous in public environments in which the audio tones may prove indiscernable or embarressing to the user. Microprocessors 86 and 88 select electrical stimulation signal parameters in accordance with the input proportional and functional selection signals and in accordance with patient parameters retrieved from memories 90, 92, 94, and 96. The microprocessors 86 and 88 are interconnected by a processor bus to perform distributed processing operations. This enables the microprocessors to share responsibility, handle high level math, accommodate additional microprocessors for more sophisticated control functions. Output lines from the processor bus are connectable with the laboratory system C to provide an operator viewable display showing the command signals, the shape and characteristics of the signals that are being sent to the nerves, and the like. The appropriate stimulation electrical signal is conveyed through an input-output port 98 to an output means 100. The output means 100 includes a plurality of radio frequency transmitters in the preferred embodiment. In another embodiment, the output means applies the selected stimulus signal directly to the electrodes through a percutaneous interface.

A cable identification means 102 determines which cables are interconnected with the portable unit. In the preferred embodiment. The portable unit B serves as both an exercise system as well as a functional system. Electrically induced exercise enables the muscle strength and fatigue resistance to be increased. In the exercise mode, the input command controller A is disconnected or disabled. In the preferred embodiment, the exercise mode is selected without external switches by merely disconnecting the cable to the input command controller and completing the connection with the implanted electrodes. The exercise algorithm allows the grasp to be ramped open, closed, and held at particular values. Alternately, the exercise algorithm can cycle between two or more grasping patterns and turn on and off in a preset time cycle. A typical exercise regime, which is applied throughout the night while the patient is sleeping, provides a 50 minute period of alternating grasp modes and a 10 minute rest period.

A power management means 104 controls the power sources which power the portable unit. In particular, the power management means monitors whether the portable unit is connected with line power, the level of charge in rechargeable batteries, and the presence of servicable batteries. The power management system selects which of the available power sources are to be utilized. If rechargeable batteries and line power are both available, the power management initiates the recharging of the rechargeable batteries. If a power cable should be pulled out or if a battery should run down, the power management system automatically changes to another power supply.

A watchdog timer 106 monitors for system problems and shuts the portable unit off if a problem arises. In particular, the microprocessors cycle through the program at predictable intervals. The watchdog timer monitors the cycles and if a cycle fails to come in the appropriate period, a software problem is assumed and the system is shut off.

With reference to FIG. 8, the stimulus pulse train signal which is applied to the electrodes E includes a series of biphasic pulses 110. Each pulse has a pulse width 112 and an amplitude 114. The leading edges of adjacent pulses are separated by an interpulse interval 116. A short interpulse delay after each stimulus pulse, an opposite polarity pulse 118 is applied to the electrodes. The delay prohibits repolarization of the active nerve fibers. The amplitude and duration of the opposite polarity pulse are selected such that the net charge transfer of the reverse polarity pulse is some proportion of the stimulation pulse, usually zero. Zeroing the net charge transfer helps prevent tissue damage with long term usage.

With reference to FIG. 9, the functional interrelationship of the parts of FIG. 7, particularly the function of the microprocessors and other software are explained in greater detail. A selected motor function decoder 120 determines the selected motor function indicated by the function selection signal and enables one or more of a plurality of electrode stimulation signal parameter selection means or channels 122. For example, a selected motor function may require the stimulation of a preselected subset of the implanted electrodes. The selection of a freeze or hold function may be implemented by holding or freezing the command signal such that the signals controlling the positions of the patient's hand or arm remain fixed.

In the preferred embodiment, each of the stimulation parameter selection means or processing path is the same construction. Specifically, each stimulation parameter selection means includes an amplitude algorithm 124 which selects an appropriate amplitude 114 of the stimulation pulse in accordance with the proportional signal. In the preferred embodiment, the amplitude algorithm means 124 is a 1 byte×256 memory or look-up table. Each of the 256 memory positions are preprogrammed to be retrieved by a corresponding one of 256 processed proportional signal levels. An amplitude index means 126 addresses the corresponding input of the amplitude look-up table.

An interpulse interval algorithm means 128 including an interval index means 130 provides an appropriate interpulse width for each level of the proportional signal. The interval algorithm means 128 is again preferably a 1 byte×256 memory or look-up table. A pulse width algorithm means 132 including a pulse width index 134 select an appropriate pulse width 112 in correspondence with the proportional signal. The pulse width algorithm is again preferably a 1 byte×256 memory or look-up table. The relationship between the proportional signal and the selected amplitude, interpulse interval, and pulse width vary from patient to patient. Further, these relationships vary as the patient develops increased muscle tone and strength through increased exercise of the stimulated muscles. Accordingly, the values in each of the look-up memories are loaded and readjusted by the cenral control system C for each patient and fine tuned for each patient periodically.

When the stimulation system D is implanted, the amplitude, interpulse interval, and pulse width parameters are conveyed to a radio frequency encoder 136 which encodes a radio frequency carrier signal with the selected electrode number, the amplitude, the interpulse interval, and the pulse width information. The transmitter 100 transmits the encoded radio frequency signal to the implanted stimulator system D. In the preferred embodiment, the radio frequency encoding scheme includes both digital and analog encoding. The electrode number is digitally encoded by periodically blanking the radio frequency signal to provide a digital representation of the electrode number to which the current is to be applied. The amplitude is also encoded digitally. In the preferred embodiment, two digital pulse spaces provide an encoding scheme to select one of 32 amplitude levels. The pulse width is encoded with an analog encoding scheme in which the width of an off portion of the RF carrier signal is indicative of the pulse width. The interpulse interval is selected by the frequency or periodicity with which the parameters are transmitted. That is, the interpulse interval is controlled by the frequency with which the RF carrier is encoded. If the stimulation pulses are channelled directly to the electrodes, the stimulus or a pulse train generator D may be carried with the portable unit B. The stimulus generator assembles a pulse train with the selected amplitude, interpulse interval, and pulse width.

The system may be operated in an open loop mode as described above. Alternately, closed loop operation may also be provided. A position or movement monitor or transducer 140 monitors the movement, position, or degree of extension or flextion of the limb or digit to be moved. Analogously, a force monitor or transducer 142 monitors the force with which the fingers or other limbs or digits are contracted or extended. It is to be appreciated that even the simplest limb movement involves the operation of two antagonistically operated muscles. A first muscle or group of muscles operates to move the skeleton in one direction while a second muscle or group of muscles provides an antagonistic or counter force. When the forces balance in three dimensions, the limb is held stationary. When one force exceeds the other, the limb moves in the direction of the predominant force vector. The stationary position or motion is controlled by the difference between these antagonistically applied forces. Although the relative forces applied by the antagonistic muscles may be relatively high or relatively low, only the difference in the forces is observed by the position or motion transducer.

With reference to FIG. 10, an exemplary position and force diagram is presented for gripping an object between the thumb and the knuckle of the forefinger. The proportional signal starts at one extreme indicating the hand is fully open or extended, generally in a handshake position, on the left side of FIG. 10. As the proportional signal progresses to the other extreme on the right side of FIG. 10, the position of the fingers contracts generally along curve 144. That is, the fingers start with no flextion and progressively flex until a fist position is reached at position 146. Thereafter, the fingers cease becoming more flexed. The thumb starts fully raised or fully flexed. At a point 150, the thumb commences becoming less flexed, i.e. approaches the forefinger. At a point 152, the thumb contacts the forefinger and stops flexing. The force with which this thumb moves is illustrated by curve 154. In the illustrated embodiment, the thumb moves toward the forefinger with relatively little force until the thumb and forefinger contact point 156. Thereafter, the force is increased by causing the appropriate muscle to contract more strongly until a maximum force or grip is reached at point 158. In the illustrated embodiment, the force with which the fingers contract is illustrated by curve 160. In the illustrated embodiment, the fingers contract with relatively little force until the thumb contacts the forefinger. Thereafter, the finger or squeezing force is increased to a higher level. Other relationships between thumb and finger force and position may, analogously, be plotted. Similarly, relationships of position and force between the fingers and thumb when performing other functions or for other limbs may be plotted.

With reference again to FIG. 9, in the closed loop system, a force and position look-up table 162 is preprogrammed with the selected relationships between the proportional command level and various finger or thumb positions and forces. For example, the look-up table 162 may be programmed in accordance with the graphs of FIG. 10. A force comparing means 164 and a position comparing means 166 compare the actual position and force monitored by position and force monitors 140 and 142 with the preselected position and force values retrieved from look-up table 162. A force index adjusting means 168 and a position difference index adjusting means 170 adjust the index means 126, 130, and 134 of the active channels until the difference between the selected and actual position and forces are optimized. The position and force difference adjusting means may simply step the appropriate index or indices up or down as may be required to bring the actual and selected force or position into coincidence. Alternately, programming logic may be provided to bring the force or position into coincidence more precisely. For example, large differences and small differences may be programmed at different rates to prevent overshoot or oscillating about the preselected position or force.

As yet another option, a sequence control means 172 may be provided for causing a preselected sequence of muscular movement and forces. For example, the preselected forces and positions of FIG. 10 may be progressively addressed out to the force and position comparing means 164 and 166. The proportional signal may be used to control the rate at which the addressing out progresses. It is to be appreciated, that the sequence may be used with the open loop system as well as with the closed loop system.

With reference to FIG. 11, the instrumentation and processing required for functional neuromuscular stimulation orthoses can be separated into several conceptual stages. A first stage 180 is to transduce and process commands to provide parameters suitable for planning a desired movement. These parameters specify the type of movement to be executed as well as movement parameters such as the magnitude or velocity. The first stage of processing may range from simple gain or offset changes to accessing transformations, signal filtering, and quantitization of continuous commands.

A second stage 182 is the planning of movement based on the control parameters. The second stage specifies the joint angle trajectories and applied torques. These movement parameters are used by a third stage 184 which coordinates and regulates the process to specify the stimulus parameters to be applied by the stimulus generator D to the muscles.

If a closed loop control sequence is implemented, a force and position monitoring stage 186 monitors the forces and positions achieved by the user. A feedback stage 188 converts the sensed force and position information into a map of actual physical movement for comparison with the planned movement parameters. Deviations between magnitude of movement, velocity of movement, trajectory, end position, and other movement parameters are used to adjust the planned movement parameters and the stimulus.

With reference to FIG. 12, the hardware for the laboratory system C includes a central processing unit 190. An analog to digital converter 192 converts the analog output of potentiometers 194 of a joystick, such as the joystick of the input control means A to digits. The potentiometers 194 may be attached to the patient or may be available to the operator. For example, the amplitude of the stimulus pulses can be set manually by the operator on potentiometers 194. Force and position monitoring transducers 156 also produce analog output signals indicative of patient motion and force. The position and force analog signals are converted with the analog to digital converter 192 and a digital input means 198 to an appropriate input for the central processing unit.

A digital output device 200, a microprocessor based pulse width and interpulse interval modulator 202, and output stages 204 provide a biphasic current pulse train to the electrodes to stimulate the patient. The stimulus pulse train, as illustrated in FIG. 8, has a rectangular cathodic phase followed by an anodic phase generated by capacitive discharge through the tissue. An interphase delay on the order of 0 to 100 microseconds between cathodic and anodic phases has been found to be a value which allows an action potential to develop but which reduces potential tissue damage. If the delay between the two phases is too small, the nerve may repolarize prior to developing an action potential. If the delay is too long, the biproducts and discharge transfer at the electrode surface may diffuse away from the electrode. The biphasic stimulus insures charged neutrality for minimal tissue damage.

The microprocessor based modulator 202 stores stimulus information descriptive of the stimulus to be applied to the electrodes. The same stimulus or pattern is repeatedly applied to the electrodes until the central processing unit 190 reprograms the modulator memories. In this manner, only changes need be communicated to the modulator. More specific to the preferred embodiment, the modulator allows the flexible formation of stimulus groups, i.e. one or more stimulus channels that operate at the same interpulse interval. The modulator stores the number of stimulus groups within the stimulation system, the stimulus channels belonging to each group, the interpulse interval for each stimulus group, and the stimulus pulse duration for each stimulus channel. In this manner, stimulus pulse trains may be applied by each electrode at a faster rate than would otherwise be permitted by the speed of the central processing unit.

The pulse width, current amplitude, and the interpulse interval modulation can be controlled independently for each electrode. This allows modulaton of the muscle force by recruitment (pulse width or amplitude) and by temporal summation (interpulse interval). In a preferred intramuscular stimulation embodiment, pulse widths on the order of 0 to 255 microseconds may be selected with a resolution of one microsecond. For other applications such as direct nerve stimulation, surface stimulation, and the like, other appropriate pulse widths ranges, interpulse intervals, amplitudes, and resolutions may be selected. The stimulus timing is controlled by the software which is discussed below.

Other peripheral hardware includes a feedback generator 206 for providing audio, electrocutaneous, or other feedback to the patient regarding the operation of the system, e.g. whether the system is active, etc. A digital plotter 208 and a printer 210 provide a hard copy of the data and parameters. A graphics storage oscilloscope 212 and a video terminal 214 provide the operator with appropriate information, such as stimulus signal strength and parameters, patient position and response, system functioning and parameters, and the like.

The software provides the intelligent decision making capability of the stimulation system. The software may be divided into four main sections. The first section provides the operator with methods to examine and specify the operation and configuration of the system. The remaining three sections are real time processes that convert the input command signals to control parameters, process the control parameters to specify stimulus parameters, and activate the external hardware to generate the stimuli. The operator interaction system is streamlined for ease of use with many different uses or subjects. The operator may specify the channels of stimulation. The stimulation channels may be organized into groups for sequential stimulation. Channels within a group are activated in a fixed sequence. For a constant interpulse interval, the phasing of one channel with respect to the next may be determined by dividing 360° by the number of channels in the group. Optionally, the channels may have selected non-uniform relative phases. The group organization also allows sequential stimulation in which portions of single muscle or muscle synergists are activated at a low frequency, out of phase with each other. Because the forces ellicited by the individual channels sum at a joint, a fused response can be maintained at a lower stimulus frequency on each channel than would be possible with a single channel scheme. This reduces fatigue. Channels may also be activated pseudo-simultaneously by putting them in separate groups with the same input control signal and the same relationship between the control signal and the interpulse interval.

The relationship between the control signals and the stimulus parameters may be specified for each channel. The system allows a non-linear pulse width and interpulse interval modulation to correct for non-linear modulation of muscle force by recruitment. Piecewise linear relationships can be specified between a single continuous control signal and the interpulse interval and the pulse width of each channel. The coordination of different muscles is achieved by specifying stimulus modulation of stimulus parameters in different channels by the same control signal.

The piecewise linear relationships may be specified by the end points of individual linear segments. These end points can also be specified or altered while stimulation is taking place by assigning the control of the individual channels to specific potentiometers on the analog to digital interface. A separate command channel can control the interpulse interval modulation and another command signal can be assigned to control pulse width modulation for each channel. One or more channels can be controlled independently of the others so that its contribution to the coordinated movement can be assessed or altered. When the stimulus parameters for that channel are appropriate, as assessed by visual monitoring or measurement of the movement or force, that combination of stimulus parameters can be entered automatically as one of the end points of a linear segment.

Command input information, stimulus parameters, patient information, data about the test and muscle being stimulated, electrode information, and general comments can be entered and stored in a secondary storage medium 216. This enables the system to be used as a notebook. The notebook information may be printed out or recalled automatically to facilitate set up in subsequent tests with the same patient.

The operator can display graphically the relationships between the command signals and the stimulus parameters in several ways. These relationships can be plotted on the storage graphics oscilloscope 212 or plotted as hard copy on the digital plotter 208. A less detailed display is available continuously on the video terminal 214. The range of pulse width and interpulse interval modulation is displayed as a function of the command input for each channel. This display allows the operator to see the relationship between pulse width and interpulse interval modulation on one channel as well as with respect to other channels. This information enables the operator to assess which muscles are coactivated.

With reference again to FIG. 11, the command processing section 180 of the software is a real time process which converts one or more input command sources into control parameters. The purpose of this process is to translate external command signals from their raw form into an internal digital parameter suitable for specifying stimulus parameters. The command processor has been designed to accept one or more analog input signals as the command storage. Accordingly, most any command source may be made compatible with the system. Suitable command sources include joint positions, myoelectric signals, or contact information.

The assignment of command inputs to the control of the individual channels or groups of channels can be accomplished as described above. However, more accurate inputs can be obtained than the command input as received from the transducer 196. The processing provided by this section of the program converts the information to the proper form. Several operations may be performed on the input command. The processing of the preferred embodiment converts command information derived from the shoulder position of the patient obtained from transducing elevation-depression and protraction-retraction movements of the patient. The position command of one axis is used as the proportional control parameter and the velocity movement of an orthogonal axis is used to initiate a logic function. First, the program provides a transformation for linearizing the output of the transducer by projecting its spherical image into x, y coordinates.

The signal is further processed to translate the transducer axes into perceived patient axes. This allows for compensation for the patient's actual shoulder movements and also may allow for the use of axes which are not truly orthogonal. The signal is scaled to match the full range of the patient's shoulder movement to the internal control parameters in order to maximize resolution in the command process. Re-zeroing or nulling specifies an arbitrary level of a command that the patient wants to use as a reference for movement. This allows the patient to select any value in the command range as the null or zero point. In the subsequent section of the program, this null point may be set to correspond to a specific point in the range of control parameters. For example, the null point may be set to correspond to the middle of the control parameter range so that movements in one direction can be used to perform a function different from movements in the opposite direction.

Hold processing enables the present control parameter level to be maintained despite subsequent changes in the command on the proportional axis. In the preferred embodiment, the velocity on the logic axis is compared with a preselected level to determine whether the control output should be held at a constant value. In this manner, the patient may move his shoulder suddenly to initiate the constant value mode. The patient may regain control by again exceeding the velocity threshold and returning command to the proportional command axis. A time delay in the proportional axis creates a lag between the logical axis and the proportional axis to insure that inadvertent movement does not alter the control output of the proportional axis prior to the hold command. The time delay is a software adjustable parameter which is a function of the ability of the subject to separate the proportional control axis movements and the logical signal axis movements from one another.

The movement planning and coordination section 182 translates the control parameter(s) that is produced by the command processor into a set of stimulus parameters that correspond to each control parameter level. The piece-wise linear modulation process is simplified by the use of look-up tables. In the preferred embodiment, the input control parameter is treated as having eight bit resolution and one 256-element integer array as allocated for the pulse width modulation for each channel and one 256-element integer array as allocated for the interpulse interval modulation of each group. The contents of each pulse array are filled during the parameter setting procedure and the values are loaded into the microprocessor based modulator to produce a desired pulse width corresponding to each possible value of the command. The contents of each interpulse interval array are the actual interpulse intervals to be set to the stimulus timing process of the stimulus generator D. The contents of these arrays, when finally adjusted, are loaded in the look-up table 124, 128, and 132 of the portable unit B.

The movement coordination and regulation process 184 runs in a continuous loop which runs whenever the command process and stimulus timing process are not being serviced. Each time through the loop, the input control signal level is used as an index to the look-up table for each of the channels and groups in use. The contents of the pulse width look-up tables at that entry are then loaded into the microprocessor based modulator. The movement planning and coordination process also checks for instructions that are entered at the terminal by the operator and updates the display of stimulus parameters on the terminal.

The fourth or stimulus processing stage controls the stimulus timing for each of the groups. The timing can be communicated to the electrodes either with an implanted stimulator or a percutaneous system implemented with output stage modules. Communication of stimulus information from the computer is carried over a parallel interface. One or more stimulus channels are provided, each of which operate at the same interpulse interval. The coordination and regulation stage 184 indicates the electrodes which are within each stimulus group, the channels which belong to each group, the interpulse interval for each group, and the stimulus pulse durations for each channel. The stimulus generator stage stores the received information and repeatedly stimulates the electrodes in accordance with the stored information. The coordination and regulation stage 184 as necessary changes the stored information to change the stimulation parameters. Stimulus information is updated as needed, allowing complete modulation of all group interpulse intervals and individual channel stimulus pulse durations.

Figure 13:
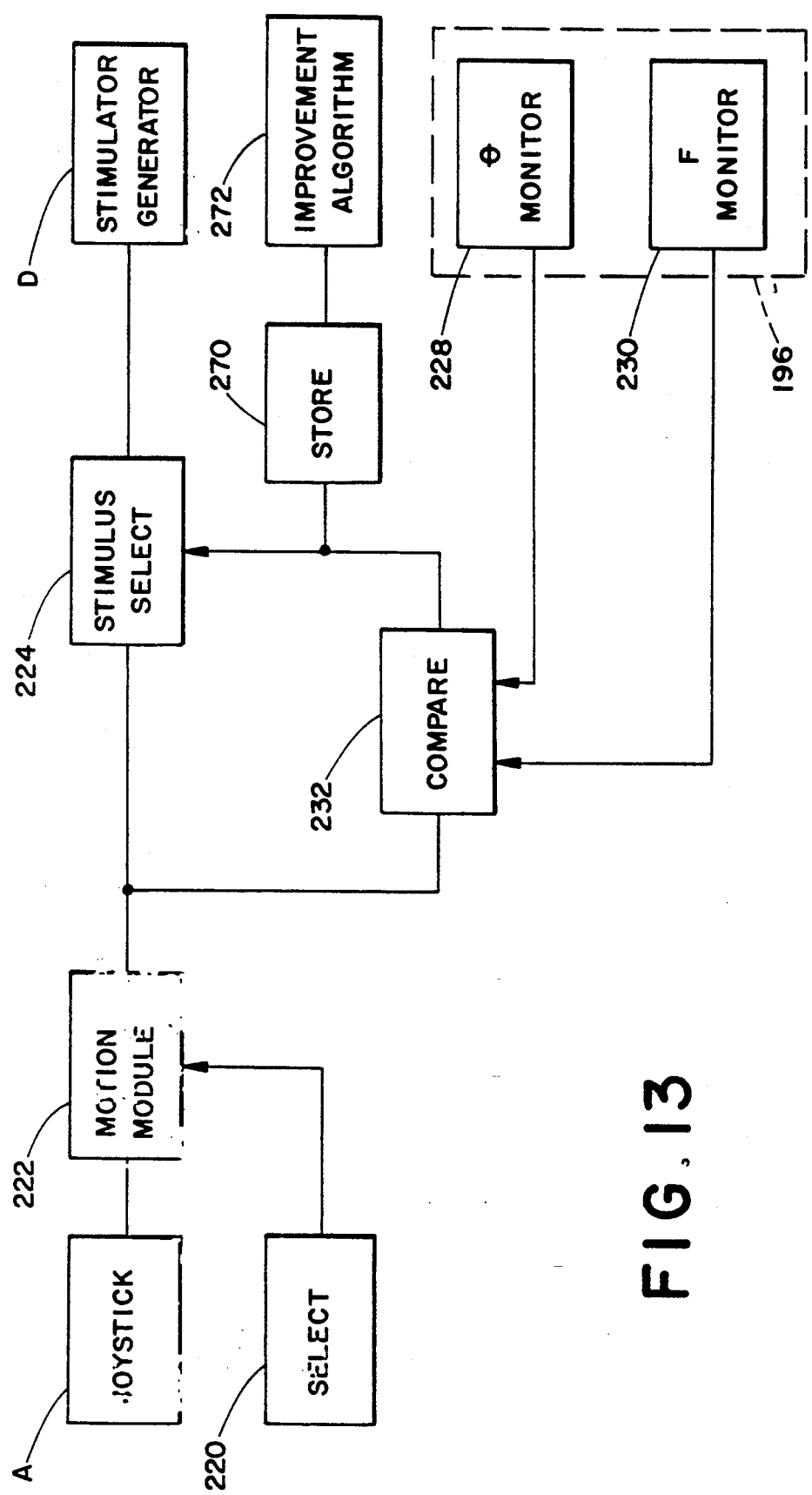

With reference to FIGS. 6 and 13, the software creates a model of the position and force for a selected movement and sets appropriate stimuli. As the patient practices the motion, the patient's muscle tone improves and the response of the muscles to a given stimuli changes. To this end, the laboratory system is periodically used to adjust the portable system of the patient for desired performance. A function selection means 220 selects an appropriate motion of the patient to be fine tuned. A motion module 222 selects the appropriate force and position for each muscle while performing the movement, as shown for example in FIG. 13. A stimulus selection means 224 formats an appropriate stimulus to achieve the selected motion. In particular, the stimulus selection means 224 selects the amplitude, interpulse interval, and pulse width to be stored in the portable, patient carried unit B. A stimulus generator D applies the selected stimulation pulse train.

The actual position and force achieved by the patient as the movement is monitored by empirical observation or by a position monitor 228 and a force monitor 230. A comparing means 232 compares the actual position and force from the monitors with the select position and force from the motion model module 222. Any differences between the position and force alter the selected stimulus pulse train parameters accordingly. This process is iteratively repeated readjusting the control algorithms until an optimum match is achieved. The reoptimized control algorithms are loaded by the microprocessor based stimulus selecting means 224 into the control algorithm memory 60 of the portable unit B. This match reoptimize is repeated periodically to maintain the patient operating at the best possible mode.

Figure 14:
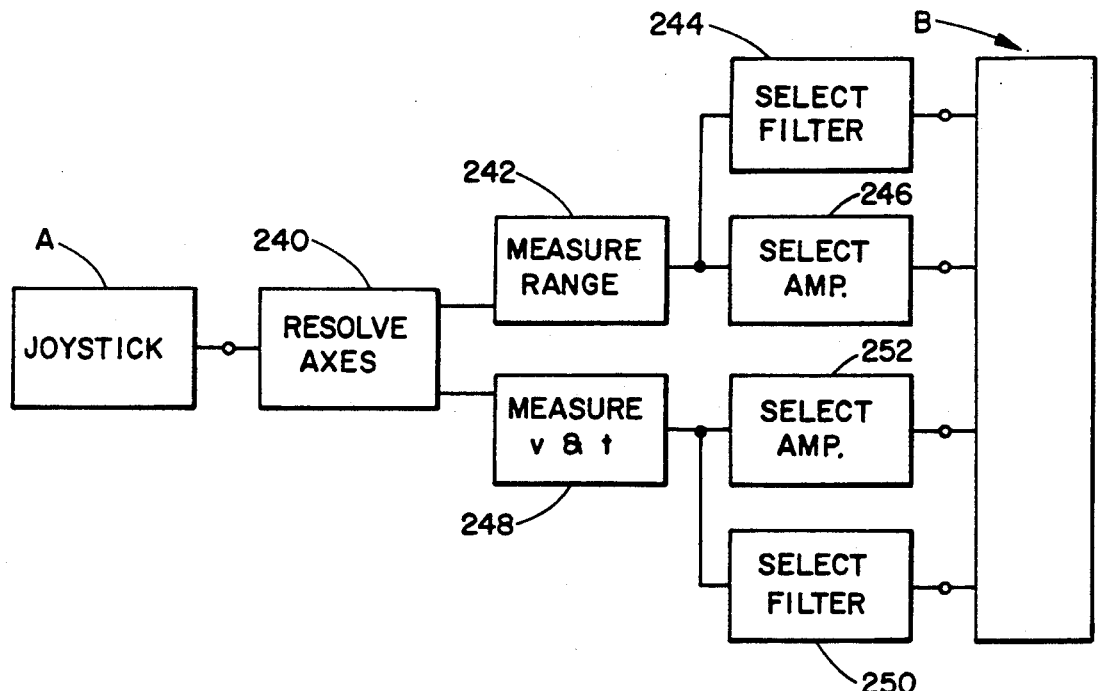

With reference to FIG. 14, a preferred upper body control input command to control processing schemes is illustrated. The command input means A is mounted to the patient and connected with the laboratory unit. As the patient moves his shoulder or other portion of the anatomy to which the input command means is attached, an axis resolving means 240 determines and resolves the proportional instruction axis and the function selection or logic axis. As described above, it is advantageous to select the proportional control along an axis over which the patient has relatively large and relatively accurately controllable range of motion. Because the logic or function selections are carried out in the preferred embodiment by sudden movements, it is advantageous to select the function or logic selection axis as one over which the patient can move his shoulder rapidly a significant distance. As also indicated above, it is advantageous for the axes to be othogonal to avoid cross-talk. However, limited amounts of cross-talk may be satisfactorily removed with appropriate filtering, signal analysis, and the like.

A range of movement measuring means or step 242 measures the patient's range of movement along the proportional axes resolved by the axes resolving means 240. A filter selecting means or step 244 monitors the smoothness or degree of accuracy with which the patient moves along the proportional axis. A filter function is selected which removes unevenness or lack of coordination or control by the patient as he moves along the proportional axis. An amplitude selection means or step 246 selects an appropriate output signal amplitude for each position along the range. The amplitudes are selected in the preferred embodiment to provide a linear relationship between the output and motion. However, other relationships may be provided as is appropriate. For example, for some applications, it may be advantageous to have more precise control at one end of the range. To achieve more precise control, a greater range of movement may be required for a corresponding change in the signal.

A velocity and time measuring means or step 248 measures the velocity and duration over which the patient can move his shoulder along the logic axis. A filter selection means or step 250 selects an appropriate filter to remove incidental movements which are smaller than the readily obtained velocity and time movements in order to inhibit false signals. An amplitude selecting means or step 252 selects appropriate on/off amplitudes to indicate that the patient has selected a change in the command function. Again, the amplitude and filter functions are periodically re-evaluated as the patient becomes more adept. The selected amplification, velocity threshold and axes, and the like are recorded in the portable patient carried system B.

Figure 15:
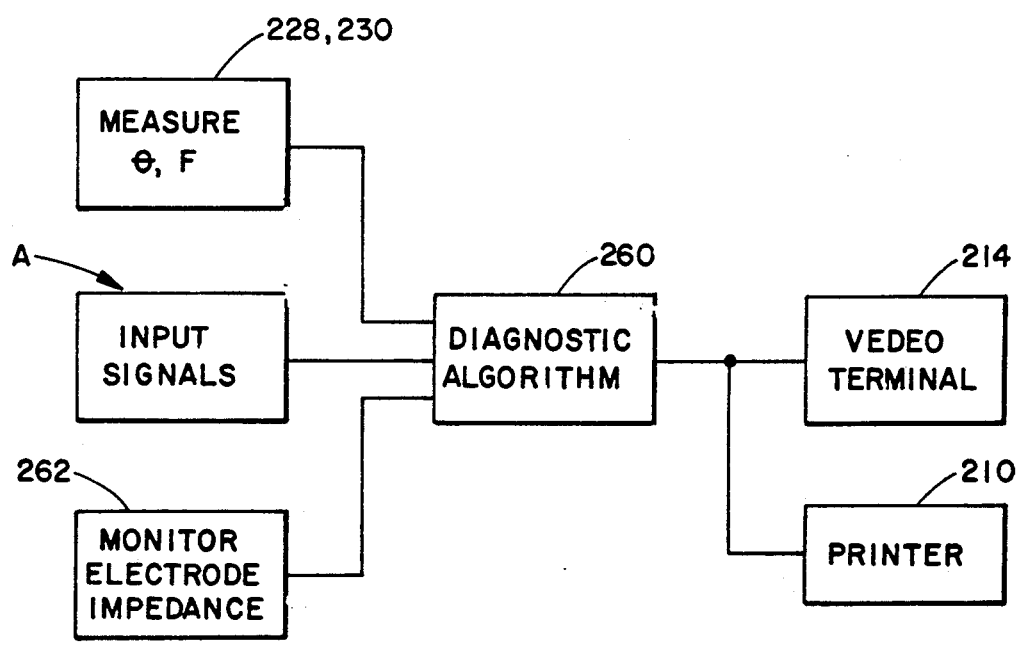

With reference to FIG. 15, the data collection/system evaluation portion of the system determines whether the system is working properly and if not, diagnoses what is wrong. A diagnostic algorithm 260 monitors and compares the input command signals from the input means A with the measured position and force of the patient. When the two become inconsistent, an appropriate diagnostic correction is determined for display on the printer 210 or video terminal 214. For example, the diagnostic algorithm looks for intermittent, large differences between the measured and commanded positions and forces. As another example, the diagnostic algorithm looks for a gradual shift in the two over time which would be indicative of muscle tone improvements by the patient which show that recalibration is required.

An electrode impedance monitoring means or step 262 monitors the impedance across each electrode. Changes in the wave form of the impedance are indicative of system failures. For example, a sudden jump in the impedance may indicate a break in the electrode or lead wires thereto.

With reference again to FIG. 13, a memory means 270 periodically stores the differences between the motion model and the actual motion and force achieved. An improvement algorithm 272 analyses the differences stored over a long period of time to determine whether the patient is becoming more proficient. The improvement algorithm determines monitoring whether the patient and the system are able to work together to achieve repeatable and stable results. The improvement algorithm determines from this information whether the system needs adjustments and refinements and how well the patient is performing over time.

With further reference to FIGS. 6 and 12, the central processing unit 190 further performs motoric and neurological assessment procedures. These procedures determine whether a person is a candidate for the program. In this procedure, an analysis of the nerves which are still intact and functioning in the affected limb to be controlled are determined. Surface stimulation is applied to corroborate which nerves are intact. The range of motion over which the limb can be articulated are measured and evaluated. A sensory evaluation determines the extent of sensory feedback or feeling in the limb. Commonly, patients with a damaged spinal column are spared the loss of some sensation in the limb providing the patient with a limited amount of feedback. This system also determines the level of voluntary control of musculature. That is, it is determined how much the patient can do compared to a scale of a normal individual. The laboratory system evaluates this data and determines whether or not the patient is a likely candidate for the present invention.

With reference to FIG. 16, the implantable stimulator D includes an electronic circuit 290 which receives and decodes incoming stimulus information, provides output stimulus pulses to the electrodes, provides immunity from external disturbances, and maintains safe operating conditions. The electronic circuitry is packaged in a hermetic incapsulation constructed of biocompatible materials. The physical size of the packaging and the electronic circuitry is minimized to increase the flexibility in selecting implantation sites in the patient. The stimulus electrodes E each include a narrow, flexible conductive lead 292 for conducting the stimulus pulse train from the implanted electronics to the appropriate muscle group. A terminal stimulus electrode 294 provides direct tissue interface to the muscles for stimulus charged injection and subsequent charge recovery. A reference electrode 256 completes the circuit.

With particular reference to FIG. 16 and 17, the implanted stimulator obtains its electromotive power through radio frequency electromagnetic induction. In particular, the stimulus signal parameters are encoded on a 10 MHz radio frequency carrier. A receiving coil 300 is connected, analogous to a secondary coil of a transformer, with a full wave rectifier 302, a voltage limiting zener diode 304, a filtering capacitor 306, and a voltage regulator 308.

Because the efficiency of power transmission through the patient's skin is only about 30%, the power consumption requirements of the implanted circuitry are kept to a minimum. To minimize the power consumption, the circuitry 290 utilizes CMOS technology. Further, the CMOS circuitry is custom designed to achieve high density integration with a relatively small number of system components. This results in versatile circuit design with high reliability, a reduced number of fabrication procedures, and a small circuit size.

As set forth above, the modulation of the carrier pulse in the preferred embodiment is achieved by gating the carrier frequency on and off. Optionally, other conventional frequency and amplitude modulation techniques may be utilized. The control signal includes two parts, a digitally encoded portion and an analog encoded portion. Optionally, all digital and all analog coding schemes may be advantageously implemented. The digitally encoded portion carries a digital indication of which the electrode channel is to carry pulses in accordance therewith. The amplitude of the pulses is also digitally encoded. In the preferred embodiment, the pulse width is encoded with an analog encoding scheme in which the width of an off portion of the RF carrier signal is indicative of the pulse width. The frequency with which the modulated pulse packets are transmitted is indicative of the interpulse interval. In this manner, channel selection, stimulus pulse width, stimulus pulse amplitude, and stimulus pulse interpulse interval are all under external control.

A control signal recovery means 310 separates the coding pulses from the carrier signal. The digital channel number encoding is decoded by a channel decoder 312. The digital amplitude designation is decoded by an amplitude decoding means 314. The pulse width encoding is decoded with a pulse width decoder 316. An interpulse interval decoder 318 sets the interpulse interval. With the interpulse interval encoded in the repetition frequency of the control signal, the interpulse interval decoder may be a trigger circuit for triggering a new stimulus pulse in response to a preselected portion of the signal. The channel selection, amplitude, pulse width, and interpulse interval decoders are connected with an output stage 320 which creates a stimulus pulse train of the selected characteristics on the selected channel.

A voltage monitor 322 monitors the voltage of the power supply and disables the logic circuitry if the voltage should fall below a preselected level. The low voltage may be due to various factors such as antenna misalignment or low transmitted power. When the voltage returns to the preselected level, the voltage monitor 322 again enables the logic circuitry.

The power supply includes an energy storage means 330 which stores potential for applying current pulses to electrodes in each channel. Because a current pulse is transmitted for a relatively short duration of each cycle, the charge may be accumulated during the non-transmitting portions of each cycle. The charge from the energy storage means 330 is selectively conveyed to the electrodes 294 by a channel selection section 332. Current flows from the electrodes 294 to the grounded reference anode 296. A switch 334 is closed when no current is flowing between the electrodes to recharge the energy storage means 330 and is opened by the output circuit 320 during current discharge across the electrodes.

With particular reference to FIG. 18, each of the output stages provides a regulated current output for the excitation of muscle tissue followed by a current reversal to recover injected charge necessary to minimize tissue damage. During stimulation, the output circuit 320 provides a stimulus pulse to the base of a switching transistor 340 in the channel selection means 332. When the transistor turns on, a stimulus current 342 flows from an energy storage capacitor 344 through the collector to the emitter controlled by a stimulus current regulator 346 and through the muscle tissue between the electrodes. The stimulus current regulator is set by the output circuit 320 to provide the selected one of a plurality of current amplitudes. For example, a typical amplitude may be 20 milliamps drawn from the capacitor 344 of the energy storage device 330. The stimulus pulse occurs concurrently with the duration of the control command, i.e. the pulse width. At the end of the stimulus pulse, the transistor 340 is turned off, halting the stimulus current. The charge storage capacitor 344 now recharges back up to the power supply voltage. A recharging current flows through the switch 334, an isolation diode 348, and a charge regulator 350 and a reverse current 352 flows in the reverse direction from the stimulus electrode 294 to the anode 296 providing the charge recovery and completing the biphasic stimulus pulse.

The output capacitor 344 serves three functions. First, it provides a reservoir of energy from which relatively large currents can be drawn for short periods of time. Second, it provides a charge reversal and insures complete charge recovery. Third, it provides AC coupling for the stimulating electrode blocking DC current flow between the stimulating electrode and anode whether the circuit is active or dormant. The DC current blocking coupled with a maximum capacitor leakage current of 1 microamp helps prevent possible galvanic electrochemical corrosion when dissimilar metals are used for the stimulus electrodes and the anode.

Recharging current to the energy storage capacitors is limited to 0.5 milliamps for two reasons. First, it places only a relatively small demand on the RF power circuit, even when several channels are recharging simultaneously. Second, during recharge current direction is such that the stimulating electrode would undergo anodic electrochemical corrosion. The low level of the recharge current helps prevent the potential delivered to the electrode during the anodic phase from exceeding the potential at which the electrode materials may corrode.

A zener diode 354 on the base of the switching transistor 340 prevents erroneous stimulus output during powering up and powering down of the stimulator circuitry. During removal or replacement of the external powering antenna, the integrity of the control logic cannot be guaranteed as the logic supply voltage rises and falls. The zener diode prevents transistor switching until the control logic is stable.

With reference again to FIG. 16, the stimulus current regulator 346 operates on a current mirroring principle. One of a plurality of selectable reference currents is set up using one of a plurality of reference mirror CMOS transistors 360. Due to the uniformity of device characteristics on the same integrated circuit die, this reference can be used to mirror the reference current into other discrete mirror current transistors 362. By selectively grouping different numbers and geometry types of the current mirror transistors together with each reference mirror transistor, one can select a regulated current that is one of a wide range of multiples of the reference current. By selectively gating different numbers of the mirror transistors conductive, different amplitudes of the stimulus currents may be selected. In the preferred embodiment, stimulus currents in the range of 0 to 32 milliamps may be selected. To conserve power, the reference current is applied to reference mirror transistors 360 only during the output of a stimulus pluse. If all of the output stages share the use of the same current regulator, simultaneous outputs from two or more of the channels may not be obtained at their full amplitude.

When using the portable system to control a plurality of implanted stimulators, an interrogation system 370 is provided to enable the portable unit to ascertain which implanted stimulator is interconnected with each transmitting coil or aerial. On initial set up, the portable unit interrogates the implanted stimulator which is interconnected with each transmitting coil and receives an implanted stimulator indicating signal back. The portable unit switches the appropriate control circuits for each implanted stimulator into interconnection with the appropriate transmitting coil.

In the preferred embodiment, the implanted stimulator interrogation system includes an identification signal decoder 372 which decodes a command for the implanted stimulator to identify itself. In response to receiving the appropriate code, the decoder closes a switch 374 to place a load 376 having a unique characteristic across the receiving antenna 300 for a preselected duration. The load produces an observable change in the transmitter characteristics, which observable change is indicative of the implanted stimulator.

Again, the RF powering of the implanted device is accomplished by exciting the transmitting coil of a loosely coupled transmitting/receiving coil pair with an RF signal. The electrical properties of the transmitting coil are dependent primarily on the geometry and construction of the transmitting coil and secondarily the effect of coupling the receiving coil into the field generated by the transmitting coil. The degree of the effect on the transmitting coil depends on the factors that affect the secondary/receiving coil. These factors include the geometry of the receiving coil, the orientation of the receiving coil in the transmitted field, and the changes of electrical activity in the receiving coil circuit. In the preferred embodiment, it is, the changes in the electrical activity in the receiving coil that are altered by switching the characteristic load thereacross. Optionally, the self resonant frequency of the coil may also be changed. Changing either the load or current in the receiving coil or the self resonant frequency of the receiving coil causes a corresponding change in the impedance of the transmitting coil. The change in impediance can be monitored in the portable unit as a change in voltage amplitude across the transmitting coil which is readily monitored by a conventional voltage amplitude monitoring circuit.

Other implanted stimulator identification mechanisms may be optionally utilized. As one example, the load may be connected continuously across the receiving coil. As another example, the switch 374 may be opened and closed in a characteristic pattern to provide a digital or other identification signal.

With reference to FIG. 19, each implanted stimulator D is encapsulated in a sealed, implantable capsule assembly. An electronic component receiving capsule 380 is machined from solid titanium stock. The capsule has an inert gas filled internal cavity of appropriate dimension to receive the electronic circuitry 290. A titanium lid 382 is hermetically sealed to the capsule and has an exposed surface to function as an anode. At one end, the capsule defines a recess 384 with three apertures therein. The apertures receive feedthrough assemblies 386 for feeding the three leads of the receiving coil 300 into the capsule for interconnection with the electric circuit 290. In the preferred embodiment, the feed through assemblies include a non-corrosive, metal conductive pin 386 which is encased in a ceramic plug 390. The recess 384 is defined by overhanging capsule portions to protect the interconnection between the coil and the feed-through assemblies.

At the opposite end, the capsule defines another recessed cavity 392 and a plurality of apertures extending into the capsule internal cavity. The number of apertures corresponds with the number of electrodes which are to be controlled. Feed through assemblies 394 provide an electrical interconnection between the circuit 290 and lead wires 396 each extending to one of the electrodes.

The antenna 300, the capsule recess cavities 384 and 396, and portions of the feed through assemblies 386 and 394 are encapsulated in an epoxy layer 398. A biocompatible elastomeric sealant layer 400 encloses the epoxy and the titanium capsule except for the portion of the lid which functions as an anode. A resilient strain relief mounting means 402 protects the electrode wires 396 from mechanical failure adjacent the capsule. A woven dacron apron 404 is connected with the capsule to enable the capsule to become anchored into the tissue of the patient.

With particular reference to FIG. 20, the electrode leads 196 include a color encoded center strand or former 410 about which first and second multi-strand wires 412, 414 are wrapped helically. In the preferred embodiment, each wire includes a plurality of stainless steel strands which are encased in a TEFLON coating. Interstices between the wire helixes are filled with a transparent elastomeric insulator 416. A transparent, elastomeric tube 418 surrounds the spiral wrapped wires.

With reference to FIG. 21, one lead is permanently connected with the implanted module D and another lead is permanently connected with one of the implanted electrodes E. An interconnection 420 interconnects the lead from the electrode with the corresponding lead from the implanted module. This facilitates installation of the electrodes, implanted module, and leads within the patient and the replacement of electrodes should one become damaged, dislodged, or otherwise unservicable. Each lead includes a connector portion 422 of like construction. Each connector portion includes a conductive pin 424 which is electrically connected with the multi-strand wires of the lead. In the preferred embodiment, the pin is hollow and has a cutout portion 426 to facilitate access to the multi-strand wires to weld them to the conductive sleeve. An elastomeric support 428 encases a portion of the pin 424 and a cord spring 430 which abuts a beveled end of the pin to provide strain relief between the pin and the lead 396. A conductive coil 432 is dimensioned to be received in tight frictional engagement with the conductive sleeve or pin 424 of each of the connectors. Pressing the connectors together tends to expand the coil 432 enabling the pins to be more readily received. Separation of the connectors causes tension on the spring which contracts its diameter causing it to adhere more strongly to the pins. In this manner, a secure, yet flexible, connection between the connectors is provided. An elastomeric sleeve 434 is secured by sutures 436 and 438 adjacent opposite terminal ends of the connectors to provide a seal which prevents body fluids from coming into contact with the electrical interconnection.

FIGS. 22 and 23 illustrate an alternate embodiment of a patient input device A. Like the Hall effect input device illustrated in FIGS. 1, 3, 4, and 5, the input device of FIGS. 22 and 23 may be implanted or mounted externally, with the external mounting being preferred. A socket portion 450 is mounted to one portion of the patient's body. A sensing arm 452 is mounted to another portion of the patient's body which has retained voluntary muscular control relative to the portion of the body to which the socket 450 is attached. The sensing arm is connected with a ferrite core 454 which is mounted in a ball-member 456. The ball member is rotatably received in the socket 450 such that the sensing arm is free to move with two degrees of freedom.

In the preferred embodiment, a driver coil 460 surrounds the socket 450, a portion of the ball member 456, and a significant portion of the ferrite core 454. Four sensing coils 462, 464, 466, and 468 are mounted in the socket member 450 closely adjacent the ferrite core. A high frequency input signal applied to the driver coil 460 is transferred through the ferrite core 454 to the sensing coils 462–468. The relative percentage of signal transfer to each of the sensing coils varies in accordance with the proximity of the ferrite core thereto.

With reference to FIG. 24, the portable patient carried system C may be used with a direct electrical connection to the electrodes E. Such a direct connection requires electrical leads to pass from the exterior portable unit through the patient's skin to the implanted electrodes. Although the patient's skin will heal and grow up to the electrical leads, a passage is defined between the skin and the leads. As with any percutaneous structure, bacteria or foreign antibodies may invade the limb through this passage causing deep abcess, granuloma, or contact dermititis. Common clinical procedures for percutaneous structures include applying and changing dressings regularly.

A percutaneous interface structure is provided which facilitates cleansing the area of the limb around the electrode leads, which protects the lead wires from damage and catching and which protects the patient against catching the lead wires and pulling or ripping the electrodes from the implantation site. The electrodes E are connected with lead wires 292 which pass through the skin at a site 470 and which are interconnected with a multichannel electrical connector 472. The electrode lead electrical connector 472 is configured for selective interconnection and disconnection from a mating shield mounted electrical connector 474.

The shield mounted connector 474 is surrounded with an elastomeric protective shield member 476. The protective shield defines an aperture 478 surrounding the site 470. A receptacle receiving passage 480 extends from the aperture to the electrical connector 474. The passage 480 is configured to receive the connector 472 in sufficiently firm frictional engagement to render decoupling of the electrical connectors 472, 474 difficult, yet with sufficiently little frictional engagement that the connectors will decouple before the electrodes are ripped loose from the muscle tissue or other physical damage occurs. A lower surface of the passage 480 is defined by a layer 482 of the resilient material which functions as a pad or shock absorbing structure.

The shield member 476 is releasably adhered to the patient's skin such as with a layer of double stick medical adhesive tape 490, or the like. To assist in preventing decoupling, the shield member has a low profile to decrease its chances for impacting nearby structures. Further, the shield member defines a relatively flat peripheral lip 492 which tapers upward gradually from the surface of the skin. Adjacent the center, a central portion 494 projects upward from the lip with smooth rounded edges. With this configuration, any impact to the shield structure is likely to be deflected as a glancing blow which will not separate or shift the shield member relative to the patient's skin. For greater security, an overlayer of a flexible, porous medical adhesive 496 is adhered over the shield member. The overlay has an aperture 498 therein which conforms to the inner edge of the lip portion 492 such that the lip portion of the shield member is overlaid by the overlay member. The overlay member extends a significant distance outward beyond the lip member to provide a more secure bond with the patient's skin.

The electrical connector 474 in the preferred embodiment is a two sided connection and has a mating interconnection for a plug 500 which is interconnected with the lead wires from the portable unit C. The shield member defines a second passage 502 for receiving the portable unit connector 500 therethrough. In the preferred embodiment, the connectors 474 and 500 mate in a plug and socket type relationship. The plug and socket members of the connectors engage in a frictional relationship and the body of plug member 500 engages in a frictional relationship with the passage 502. The frictional relationships are selected such that the connectors become disconnected under a force which is less than the force required to move the shield member 476 relative to the patient's skin, yet hold the connectors in firm electrical interconnection at lower interaction forces.

The invention has been described with reference to the preferred embodiment. Obviously, alterations and modifications will occur to others upon reading and understanding the preceding detailed description. It is intended that the invention be construed as including all such alterations and modifications in so far as they come within the scope of the appended claims or the equivalents thereof.

Having thus described the preferred embodiments, the invention is now claimed to be:

1. A functional neuromuscular stimulation system comprising:
   a relative position sensor for sensing a relative position of a joint of a patient's body and generating electrical command signals which are proportional to the sensed joint position, the position sensor being implanted in the patient's body;
   an implanted telemetry system for conveying the command signals, the telemetry system including an encoding means which applies the command signals to a gate means which selectively applies a load across a power signal receiving antenna to modify a characteristic thereof, such that a monitorable characteristic of the power signal is modulated in accordance with the command signals;
   a transmitter means for transmitting the power signals to the receiving antenna;
   a parameter selecting means operatively connected with the transmitter means for selecting parameters of an electrical stimulation pulse train in accordance with the command signal modulated characteristic of the power signal;
   a pulse train generator means for generating a train of stimulation pulses with the selected pulse train parameters; and,
   at least a first electrode operatively connected with the pulse train generator.

2. A functional neuromuscular stimulation apparatus comprising:
   a parameter selecting means for selecting parameters of an electrical stimulation pulse train in accordance with input command signals, the parameter selecting means including a channel selecting means for selecting which of a plurality of implanted electrodes is to receive the pulse train, an amplitude means for selecting an amplitude of each stimulation pulse, an interval means for selecting an interpulse interval, and a pulse width means for selecting a width of each pulse;
   a transmitter for transmitting selected channel, amplitude, interpulse interval, and pulse width parameters received from the parameter selecting means in a carrier signal and wherein the pulse train generator includes:
      a power supply means for converting energy from the carrier signal into electrical potential for operating a pulse train generator and for providing electrical currents to the electrodes;
      a decoding means for decoding at least the encoded amplitude and pulse width from the encoded carrier signal, the decoding means including a channel decoder for decoding which electrodes are to apply each selected stimulus current pulse train, a pulse width decoder for determining the pulse width of pulses of the stimulus current pulse train, and an amplitude decoder for determining an amplitude of pulses of the stimulus pulse train;
      an energy storage means for storing electrical potential for each electrode channel;
      a channel selection means for selectively passing electrical current from the energy storage means to the electrode of the selected channel with the selected pulse width;
      a current regulator means for regulating the amplitude of the stimulus current pulses in accordance with the amplitude decoded by the amplitude decoding means.

3. The system as set forth in claim 2 wherein the pulse train generator is implanted in a patient and further including a transmitter means for transmitting the selected amplitude, interpulse interval, and pulse width to the pulse train generator.

4. The system as set forth in claim 3 further including:
   a capsule for encasing the pulse train generator and being implanted therewith;
   a receiving coil being mounted exteriorally with the capsule and being potted in an electrically transmissive medium, the receiving coil being operatively connected with the pulse train generator for receiving signals transmitted by the transmitting means; and,
   a flexible electrical lead mechanically connected at one end through the capsule into electrical contact with the pulse train generator and being electrically connected with one of the electrodes at another end.

5. A functional neuromuscular stimulation system comprising:
   an input command control means for providing an electrical command signal indicative of a selected muscular response, the input command control means including:
      a permanent magnet mounted within a ball member;
      at least three Hall-effect plates mounted in a socket in which a ball member is movably received such that as the ball member and socket move relative to each other, physical proximity of the magnet changes relative to the Hall-effect plates;
      a means for applying electrical potential across each of the Hall-effect plates in a first direction;
      a means for monitoring a potential difference across each Hall-effect plate in a direction generally transverse to the first direction, the potential difference monitoring means providing output signals which vary in proportion to the monitored potential differences, such that as the ball member and socket move relative to each other, the changes in the physical proximity of the magnet relative to the Hall-effect plates changes magnetic flux through each Hall-effect plate and the potential transversely thereacross;
      an encoding means for converting the output signals indicative of the relative position of the ball member and socket into the command signal;

at least a first parameter selecting means for selecting properties of an electrical stimulation pulse train in accordance with the electrical command signals;

a pulse train generator means for generating a train of stimulation pulses with the selected properties, the pulse train generator means being operatively connected with the first parameter selecting means; and, at least a first electrode operatively connected with the pulse train generator.

6. The system as set forth in claim 5 wherein the input command control means includes a relative position sensor for sensing the relative position of a joint of a patient's body, the electrical command signals being proportional to the sensed joint position.

* * * * *